United States Patent
Elmaleh et al.

(10) Patent No.: US 8,114,379 B2
(45) Date of Patent: *Feb. 14, 2012

(54) DIAGNOSTIC AND THERAPEUTIC ALKYL PIPERIDINE/PIPERAZINE COMPOUNDS AND PROCESS

(75) Inventors: David R. Elmaleh, Newton, MA (US);
Choi Sungwoon, Sharon, MA (US);
Alan J. Fischman, Boston, MA (US)

(73) Assignee: The General Hospital Corporation, Charlestown, MA (US)

( * ) Notice: Subject to any disclaimer, the term of this patent is extended or adjusted under 35 U.S.C. 154(b) by 643 days.

This patent is subject to a terminal disclaimer.

(21) Appl. No.: 12/100,067

(22) Filed: Apr. 9, 2008

(65) Prior Publication Data

US 2009/0191125 A1 Jul. 30, 2009

Related U.S. Application Data

(63) Continuation of application No. 10/814,118, filed on Mar. 31, 2004, now Pat. No. 7,381,822.

(51) Int. Cl.
*A61K 51/04* (2006.01)
*A61K 49/22* (2006.01)
*A61K 31/4965* (2006.01)
*A61K 31/497* (2006.01)

(52) U.S. Cl. .................. 424/1.11; 424/9.1; 514/253.01; 514/331

(58) Field of Classification Search .................. 544/360, 544/390; 514/525.12, 253.01, 331; 424/9.1, 424/1.11
See application file for complete search history.

(56) References Cited

U.S. PATENT DOCUMENTS

| | | | |
|---|---|---|---|
| 4,476,129 | A | 10/1984 | Gootjes et al. |
| 5,652,240 | A | 7/1997 | Abramo et al. |
| 6,387,389 | B1 | 5/2002 | Rothman et al. |
| 6,835,371 | B1 | 12/2004 | Elmaleh et al. |

*Primary Examiner* — James O Wilson
*Assistant Examiner* — Ebenezer O Sackey
(74) *Attorney, Agent, or Firm* — Foley Hoag, LLP

(57) ABSTRACT

Piperidine or piperazine compounds useful for treating neurodegenerated diseases characterized by the lack of dopamine neurons activity or for imaging the dopamine neurons are provided. The compounds are characterized by the formulae:

Formula I

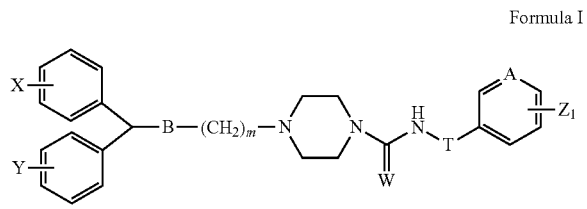

Formula II

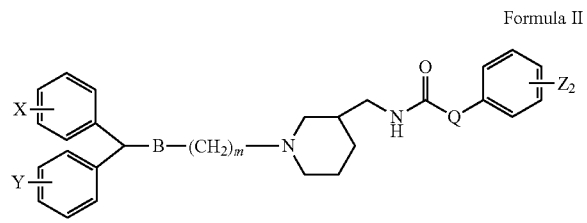

Formula III

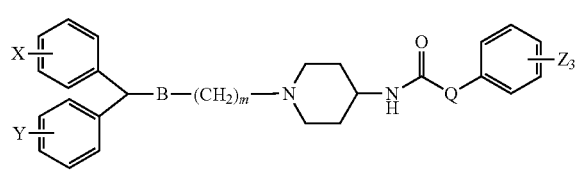

Formula IV

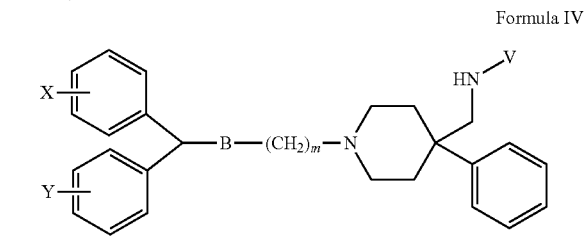

Formula V
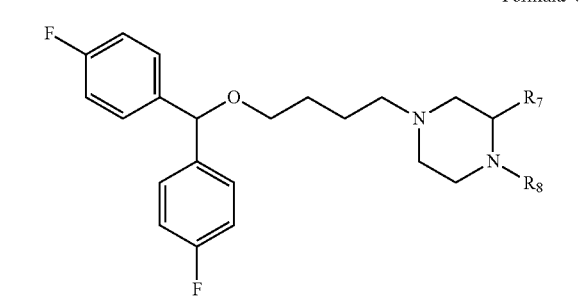

wherein:
n is an integer of 1 to 6; X, Y, $Z_1$ and $Z_2$ can be the same or different and are hydrogen, halo, haloalkyl, alkyl, aryl, ($C_1$-$C_6$) alkoxy, N-alkyl, ($C_2$-$C_6$) acyloxy, N-alkylene, —SH, —SR, wherein R is from the same group as $R_1$ and $R_2$ and can be the same or different than $R_1$ and $R_2$, amino, nitro, cyano, hydroxy, C(=O)$OR_6$, —C(=O)$NR_5R_4$, $NR_3R_2$, or S(=O)$_k$ $R_1$ wherein $_k$ is 1 or 2, and $R_1$ to $R_6$ are independently hydrogen or ($C_1$-$C_6$) alkyl;
$R_1$, and $R_2$ can be the same or different and are hydrogen, ($C_1$-$C_6$) alkyl, hydroxyalkyl or mercaptoalkyl, —C(=O)$OR_1$, cyano, ($C_1$-$C_6$) alkenyl, ($C_2$-$C_6$) alkynyl, or 1,2,4-oxadiazol-5-yl optionally substituted at the 3-position by $Z_4$ wherein any ($C_1$-$C_6$) alky, ($C_1$-$C_6$) alkanoyl, ($C_2$-$C_6$) alkenyl or ($C_2$-$C_6$) alkynyl can optionally be substituted by 1, 2 or 3 Z;

$R_7$ can be hydrogen, O or phenyl $R_8$ can be hydrogen, phenyl, halophenyl, nitrophenyl, pyridyl, piperonyl or sulfoxonitrophenyl $Z_4$ is ($C_1$-$C_6$) alkyl or phenyl, optionally substituted by 1, 2 or 3 $Z_1$ W is O or S T is amino or $C_1$-$C_6$ aminoalkyl A is N or C T is $C_1$-$C_6$ alklyl or sulfonyl and V is alkyl ($C_0$-$C_6$), alkenyl, alkynyl, haloaryl, alkyl phenol, alkyl halophenyl, and $R_1$ or $R_2$ as indicated above and φ is phenyl, naphthyl, thienyl or pyridinyl.

8 Claims, 1 Drawing Sheet

GBR 12909

Bisarylmethoxyalkylpiperidines

DIAGNOSTIC AND THERAPEUTIC ALKYL PIPERIDINE/PIPERAZINE COMPOUNDS AND PROCESS

RELATED APPLICATION

This application is a continuation of U.S. patent application Ser. No. 10/814,118, filed Mar. 31, 2004, now U.S. Pat. No. 7,381,822.

BACKGROUND OF THE INVENTION

1. Field of the Invention

This invention relates to a diagnostic and therapeutic bisarylmethoxybutylpiperazines/piperidines, their use as diagnostic or therapeutic agents and to a process for making the bisarylmethoxybutyl piperazines/piperidines.

2. Description of Prior Art

The dopaminergic (DA) neurotransmitter systems are intimately involved with a number of central nervous system (CNS) disorders including those involved with movement, e.g., Parkinson's Disease and reinforcing effects, e.g., cocaine dependency. Interest in these two disorders in particular has stimulated research efforts to develop specific agents that can be used either diagnostically, to evaluate the extent of the disease, or therapeutically to antagonize the effect of cocaine. Cocaine recognition sites are localized on dopamine nerve terminals. Drugs that bind, affect or block these sites therefore have potential uses which include: (i) imaging probes for neurodegenerative disorders; and (ii) imaging probes for dopamine transporter/cocaine binding sites. Furthermore, in many instances these compounds or analogs become active on other sites that affect the serotonergic system and, therefore, may be used to treat disorders associated with serotonin (e.g., depression, PMS, weight, or aging).

Because of the unique anatomical location of the cocaine recognition sites, a high affinity probe for imaging of these sites in vivo in the brain can be carried out using positron emission tomography (PET) or single photon emission computed tomography (SPECT) imaging. Such imaging is useful for diagnosing or monitoring the Parkinson's disease, other neurological disorders characterized by the degeneration of dopamine (DA) nerve terminals or by aging. Preferably, the common target for compounds that would fulfill these objectives is the dopamine transporter (DAT), a 12-transmembrane spanning presynaptic protein that removes the dopamine from the synaptic cleft following its release. The two classes of competitive drugs that have been most extensively examined are the stable tropane analogs of cocaine characterized by WIN 35,428 (also known as CFT) and the piperazine derivatives characterized by GBR-12935. Both exert their effect at nanomolar concentrations.

The cocaine analog, 2β-carbomethoxy-3β-fluorophenyl) tropane (CFT) and other analogs have proven to be an effective probe for studying dopamine-related diseases and cocaine binding sites in the striatum. For example, the progression of Parkinson's disease in primate models and subjects can be monitored by administering radiolabeled analogs of CFT and imaging the distribution of radioactivity in the brain. PET has been used to image $^{11}$C labeled analogs of CFT in primate models, Hantraye et al., *Neuroreport* 3.265 (1992), Farde et al., *Synapse* 16:93 (1994) while SPECT has been used to image iodinated CFT analogs in both primate models and human subjects (Shaya et al., *Synapse* 10:169 (1992) and Neumeyer et al., *J. Med. Chem.* 34:3144 (1991), Elmaleh et al, *J. Nucl. Med.*)

Various substances (particularly cocaine and cocaine congeners) are potent inhibitors of dopamine transport in the striatum of the brain because they bind to the dopamine transporter. These substances have different affinities or $IC_{50}$'s for inhibiting dopamine transport and for blocking cocaine. The more strongly these substances block dopamine transport, the more strongly they bind to sites on the dopamine transporter which have been labeled by [$^3$H] cocaine or by [$^3$H] CFT, Madras et al., (1089) *J. Pharmacol. Exp. Ther.* 251:131-141; and Madras et al. (1989) *Mol. Pharmacol.* 36:518-524. The hope that these compounds might be Parkinson's markers is further supported by the parallel between loss of binding and loss of dopamine in the diseased brain (Madras et al. *Catechol. Symp.* 193, 1992).

Because of it's widespread, low cost and simplicity, SPECT is preferred to PET for routine imaging directed towards diagnosis. Technetium-99m is the tracer of choice for SPECT imaging because of its excellent physical characteristics and widespread availability. Recently, technetium-99m CFT analogs were reported which appear to be extracted by the brain and concentrate preferentially in its dopamine rich regions (Madras et al., *Synapse* 22:239 (1996) and Meegalla et al., *J. Am. Chem. Soc.* 117:11037 (1995).

There is need for improved diagnostic agents and markers of neurogenerative disorders, which have unproved specificity for concentrating in dopamine rich regions in the brain. Such agents can provide improved diagnosis for excluding at an early stage of Parkinson's disease as the cause of symptoms, which may be useful information in diagnosing other conditions. Moreover, early diagnosis of Parkinson's disease can facilitate the introduction of putative prophylactic drug therapy (e.g., deprenyl) prior to the onset of more severe symptoms, Kaufman and Madras (1991) *Synapse* 9:43-49. Detection of nerve cell depletion in the presymptomatic phase in an animal model of Parkinson's disease would also be useful, e.g., when using the model to evaluate therapies for Parkinson's disease, Hantraye et at. (1992) *Neurol. Reports* 3:26-268; and Hahtraye et al. (1992) *Soc. Neurosci. Abstra.* 18:935.

There is a particular need for diagnostic agents and markers of neurogenerative disorders that selectively target a domain transporting protein (the dopamine transporter) in preference to another protein known as the serotonin transporter. In normal brain tissue, the dopamine: serotonin transporter density ratio is approximately 10:1. Diagnostic agents can be used to monitor the effects of Parkinson's disease therapy by determining the loss or reduction of loss of dopamine. In certain neurodegenerative disorders, such as Parkinson's disease, nerve cells that produce dopamine (and on which the dopamine transporter is located) undergo severe depletion while serotonin transporter ratio can fall to 50% in Parkinson's disease.

Accordingly, it would be desirable to provide improved diagnostic and therapeutic compositions that have improved selectivity for being concentrated in dopamine regions of the brain as compared to presently available diagnostic and therapeutic compositions. Such improved diagnostic and therapeutic compositions can provide a means for earlier detecting an abnormal condition of the brain measurable by determining the state of the dopamine rich regions. In addition, such improved therapeutic composition can provide a basis for more effective treatment of a patient such as a cocaine-dependent patient.

SUMMARY OF THE INVENTION

The present invention is based on the discovery that bisarylmethoxybutylpiperazines/piperidines derivatives have high affinity and high selectivity for dopamine transporters.

The compounds of this invention are represented by the Formulas I, II, III, IV, and V ad physiologically acceptable salts thereof:

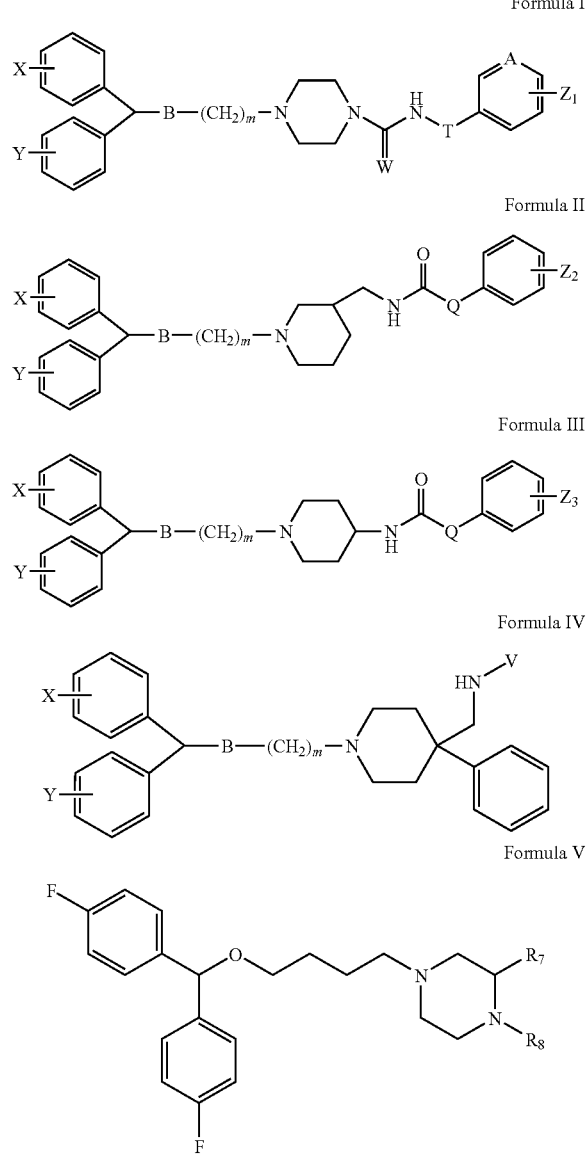

wherein:

n is an integer of 1 to 6; B can be O, N, —CONH—, or —NHCO—; X, Y, $Z_1$, $Z_2$ and $Z_3$ can be the same or different and are hydrogen, halo, haloalkyl, alkyl, aryl, ($C_1$-$C_6$) alkoxy, N-alkyl, ($C_2$-$C_6$) acyloxy, N-alkylene, —SH, —SR, wherein R is from the same group as $R_1$ and $R_2$ and can be the same or different than $R_1$ and $R_2$, amino, nitro, cyano, hydroxy, C(=O)$OR_6$, —C(=O)$NR_5R_4$, $NR_3R_2$, or S(=O)$_kR_1$ wherein k is 1 or 2, and $R_1$ to $R_6$ are independently hydrogen or ($C_1$-$C_6$) alkyl;

$R_1$, and $R_2$ can be the same or different and are hydrogen, ($C_1$-$C_6$) alkyl, hydroxyalkyl or mercaptoalkyl, —C(=O)$OR_1$, cyano, ($C_1$-$C_6$) alkenyl, ($C_2$-$C_6$) alkynyl, or 1,2,4-oxadiazol-5-yl optionally substituted at the 3-position by $Z_4$ wherein any ($C_1$-$C_6$) alky, ($C_1$-$C_6$) alkanoyl, ($C_2$-$C_6$) alkenyl or ($C_2$-$C_6$) alkynyl can optionally be substituted by 1, 2 or 3 Z;

$Z_4$ is ($C_1$-$C_6$) alkyl or phenyl, optionally substituted by 1, 2 or 3 $Z_1$ $R_7$ can be hydrogen, O or phenyl $R_8$ can be hydrogen, phenyl, halophenyl, nitrophenyl, pyridyl, piperonyl or sulfoxonitrophenyl W is O or S Q is amino or $C_1$-$C_6$ amino alkyl.

A is N or C

T is $C_1$-$C_6$ alkyl or sulfonyl and

V is alkyl ($C_0$-$C_6$), alkenyl, alkynyl, haloaryl, alkyl phenol, alkyl halophenyl, and $R_1$ or $R_2$ from previous page.

φ is phenyl, naphthyl, thienyl or pyridinyl.

The compounds of this invention are useful as diagnostic agents in their labeled form with radionuclides such as $^{123}$I, $^{125}$I, $^{99m}$Tc or the like. In their labeled or unlabeled form, the compounds of this invention are useful as therapeutic agents including being agonists, partial agonists, antagonist or partial antagonist compounds against the effects of cocaine.

The present invention also comprises a method for detecting Parkinsonism in a human patient which comprises administering to a human patient a detectably labeled compound of this invention and detecting its binding to CNS tissue such as by quantifying dopamine terminals with the compound by utilizing PET or SPECT.

The present invention also provides a method for monitoring cocaine-binding sites of the CNS such as by determining site occupancy by potential cocaine therapeutics with the labeled compounds of this invention.

In another aspect of this invention, the compounds of this invention are utilized in a method for treating neurodegenerative disorders or cocaine abuse.

Therapeutic compositions according to the invention comprise a compound as described above formulated in a pharmaceutically acceptable carrier. Such compositions can be used to selectively image cocaine binding regions of the central nervous system of a human patient by administering detectably labeled compound of this invention to the central nervous system and detecting the binding of that compound to CNS tissue by (PET) or (SPECT). Such a compounds also are useful in treatment of neurodegenerative disorders characterized by dopamine deficits or cocaine abuse and to follow the effects of therapy for dopamine or cocaine abuse.

DESCRIPTION OF SPECIFIC EMBODIMENTS

Figure 1:
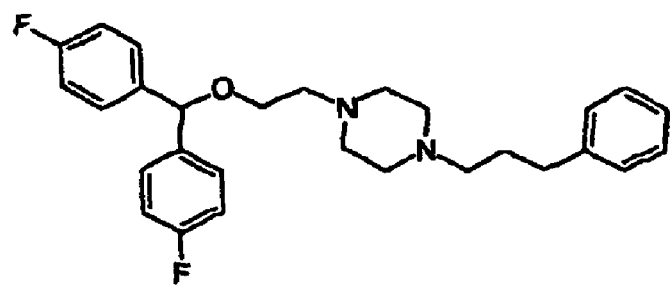
FIG. 1 depicts the structures of GBR 12909 and bisarylmethoxyalkylpiperidines.
Figure 1:
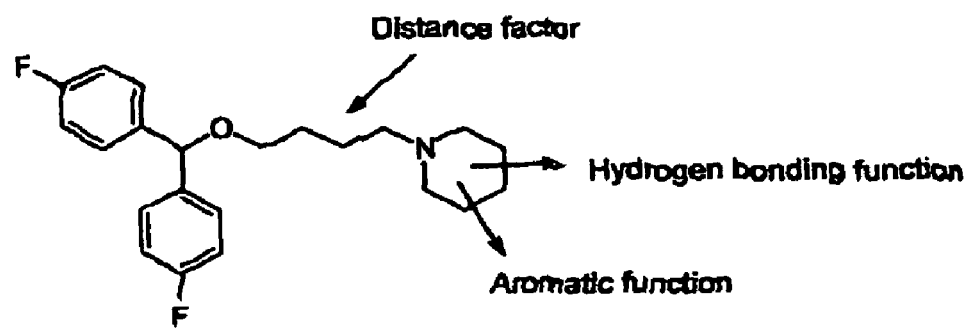

The piperidine/piperazine compounds of this invention are prepared for administration to an animal in the form of a pharmaceutically acceptable free base or a salt such as tartrate, citrate, napthalene-1.5-disulfonate, fumarate, maleate, hydrochloride or hydrobrornide salts.

The compounds of this invention can be labeled with a radionuclide by any conventional process such as when $^{123}$I or $^{125}$I which are bound to the compound at the X, Y or Z position or with $^{99m}$Tc which is bound to the compound at the X, Y or Z position or with a derivitized nitrogen such as in the positions of RI and R2.

The piperidine and piperazine compounds of this invention are useful for imaging organs containing dopamine receptors in an animal including humans. The piperidine and piperazine compounds of this invention are particularly useful for imaging dopamine neurons in the brain, for example detecting the loss of dopamine neurons in the brain. The piperidine and piperazine compounds of this invention bind the dopamine transporter with higher affinity than currently used dopamine-imaging agents. In addition, the piperidine and piperazine compounds are selective for the dopamine transporter and have good distribution to and penetration of the brain. Therefore, utilization of the piperidine and peperazine compounds may enable earlier diagnosis of neurogenerative disorders than is now possible as well as the monitoring of the effectiveness of the treatment.

Imaging dopamine neurons in the brain with the piperidine and piperazine compounds of this invention is used for monitoring the brain uptake of drugs such as cocaine or cocaine substitutes. The piperidine and piperazine compounds of this invention may block cocaine binding but permit reuptake of dopamine. The craving experienced by individuals who abuse cocaine is a result of the occupancy of the dopamine transporter by the drug. Cocaine abuse can be treated with drugs that occupy the sites associated with the dopamine transporter in place of dopamine or cocaine. Imaging of the dopamine neurons in the brain with piperidine and piperazine compounds of the invention is used to identify drugs which occupy the sites or other site of cocaine uptake and therefore have potential to treat individuals who abuse cocaine. In many instances the analog may preferably occupy sites associated with serotonin.

Administering an imaging dose of one of the radiolabeled piperidine and peperazine compounds, for example, a piperidine, can image the dopamine neurons in an individual and piperazine derivative represented by structural Formula I or Formula II. An "imaging dose" of a piperidine and piperazine compound is an amount which concentrates in an organ with dopamine neurons and which has sufficient radioactivity so that the distribution of dopamine neurons in the organ can be converted into an image by a technique such as PET or SPECT. An "imaging dose" of the piperidine and piperazine compound of the piperidine and peperazine compound of this invention typically ranges from about 0.5 mCi to about 50 mCi and with a specific activity ranging from about 1 mCi/μM to about 100 mCi/μM, preferably from about 1 mCi to about 20 mCi and with a specific activity ranging from about 10 Ci/μM to about 100 Ci/μM, but will vary according to factor such as the general health, age and sex of the individual and the particular application.

In one aspect of this invention, a method of treating a subject is provided in which a desirable therapeutic effect can be achieved by occupying the dopamine transporter receptor with an agent or drug. Suitable subjects include individuals with Parkinson's disease, brain aging, Huntington's disease, tardive dyskinesiaa and schizophrenia. The method comprises administering to the subject a therapeutically effective amount of piperidine and piperazine of this invention with a pharmaceutically acceptable carrier. A "therapeutically effective amount" is the amount, which brings about the amelioration of symptoms or slows the progression of one of the above-monitored conditions. Suitable dosages range from about 0.01 mg/kg per day to about 100 mg/kg per day. In another aspect some of these compounds show selectivity to the serotonin transporter and/or mixed activity for both dopamine and serotonin and therefore, are useful for treating disorders associated with serotonin.

The piperidine and piperazine compounds are generally administered intravenously when used for imaging dopamine neurons. An appropriate composition comprising the compound to be administered can be prepared in a physiologically acceptable vehicle or carrier. Suitable carriers include, for example, a dermal patch, aqueous or alcoholic/aqueous solutions, saline and buffered media. Intravenous vehicles can include various additives, preservatives, or fluid nutrients or electrolyte replenishers (See, generally, *Remington's Pharmaceutical Science*, 16th Edition, Mack, Ed. (1990).

When used for treatment, the piperidine and piperazine compounds of this invention can be administered by a variety of known methods, including orally or by parenteral routes (e.g., intramuscular, intravenous, transdermal, subcutaneous, nasal or topical). The form in which the compounds are administered will be determined by the route of administration. Such forms will include, but are not limited to capsular and tablet formulations (for oral administration), liquid formulations (for oral, intravenous, intramuscular or subcutaneous administration) and slow releasing micro carriers (for intramuscular or intravenous administration). The formulations can also contain a physiologically acceptable vehicle and optional adjuvants, flavorings, colorants and preservatives. Suitable physiologically acceptable vehicles may include saline, sterile water, Ringer's solution, and isotonic sodium chloride solutions.

Autoradiographic distribution of the compounds are conducted according to in vitro techniques (Kaufman et al., *Synapse* 9:177 (1991) or ex vivo techniques (Kaufman and Madras, *Synapse* 12:99 (1992)).

SPECT or PET imaging may be carried out using any appropriate apparatus. Imaging is carried out on conscious subject using standard imaging (see, e.g., *Medicine, Scientific American, Inc.*, ed. Rubenstein and Federman, 1988; Jaszczak and Coleman, Invest. Radio. 20:897 (1985); and Coleman et al., *Invest. Radiol.* 21:1 (1986).

The piperidine and piperazine compounds of this invention can be prepared as indicated in Schemes 1-4. Modifications to these syntheses to prepare compounds other than those specifically depicted can be carried out by one of ordinary skill in the art using no more than routine experimentation.

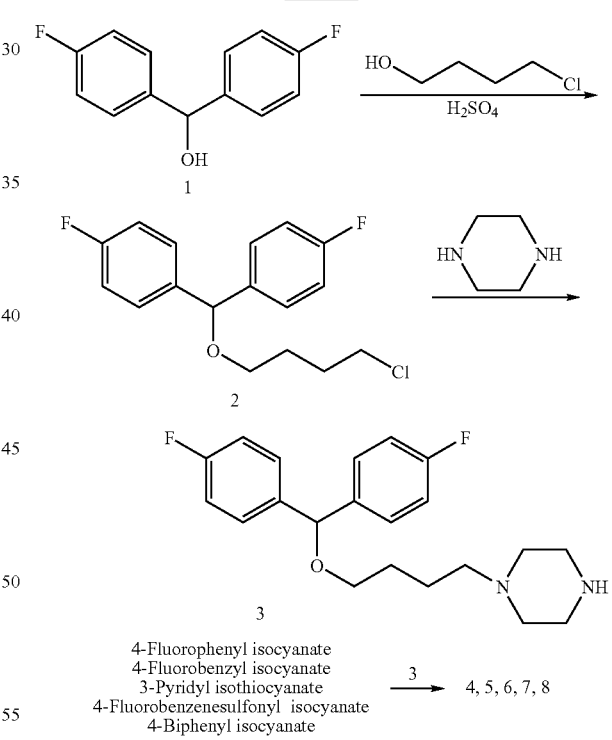

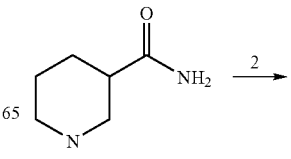

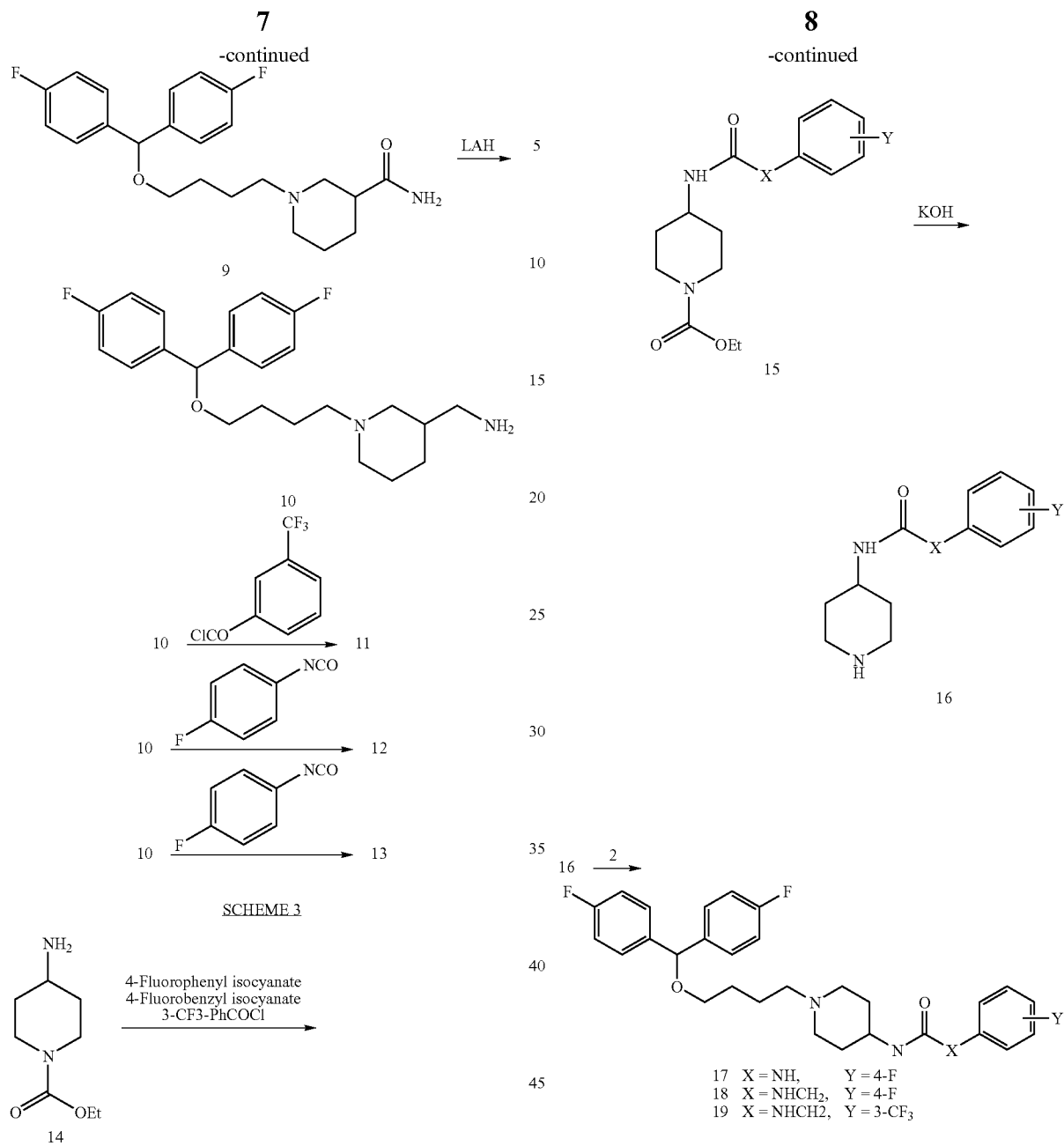
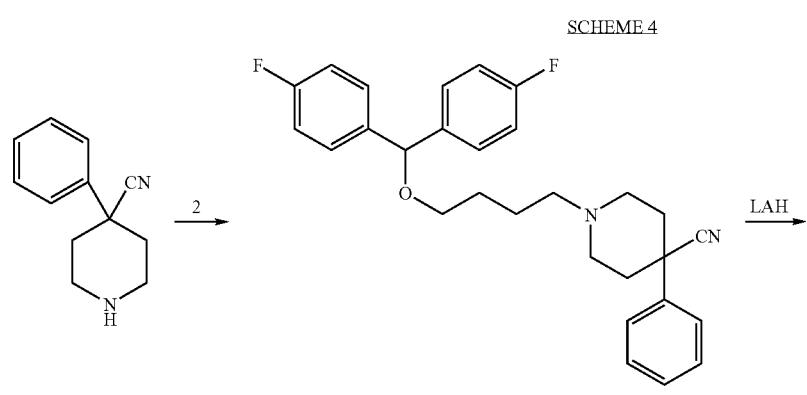
SCHEME 4

-continued

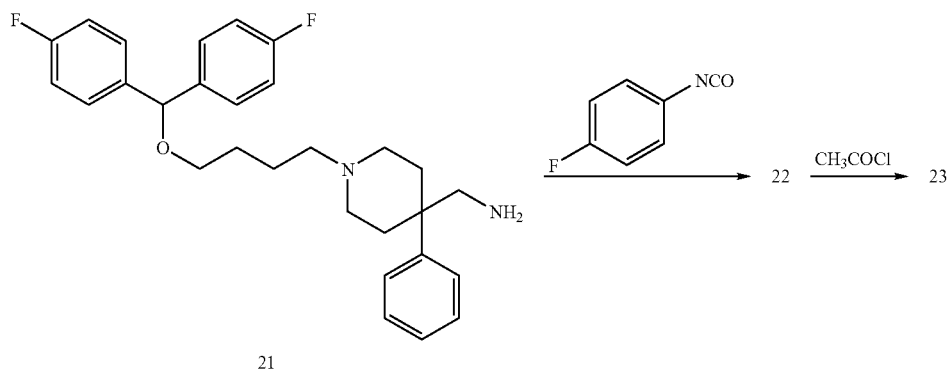

21 →(CH₃COCl)→ 22 →(CH₃COCl)→ 23

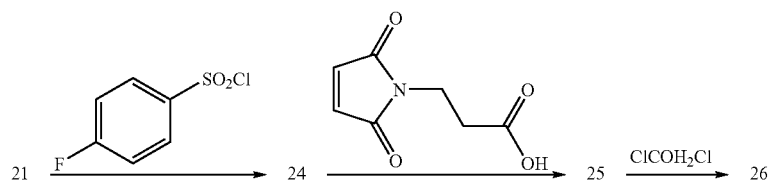

21 →(4-F-C₆H₄-SO₂Cl)→ 24 →(maleimide propanoic acid)→ 25 →(ClCOCH₂Cl)→ 26

Scheme 5

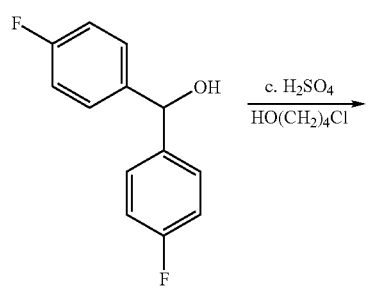

→ c. H₂SO₄ / HO(CH₂)₄Cl →

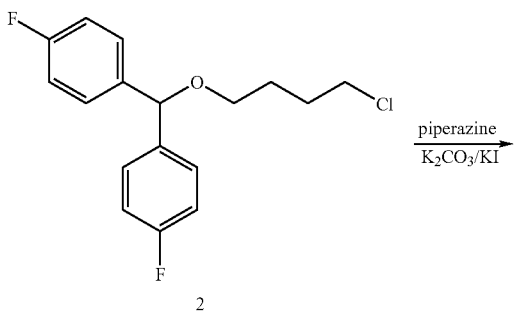

2

→ piperazine / K₂CO₃/KI →

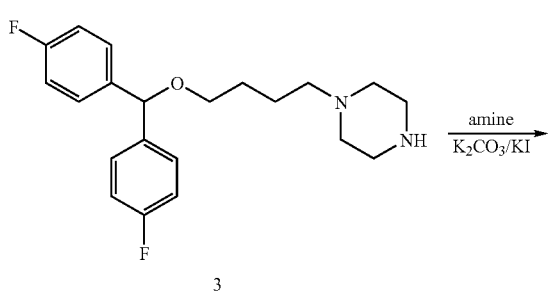

3

-continued

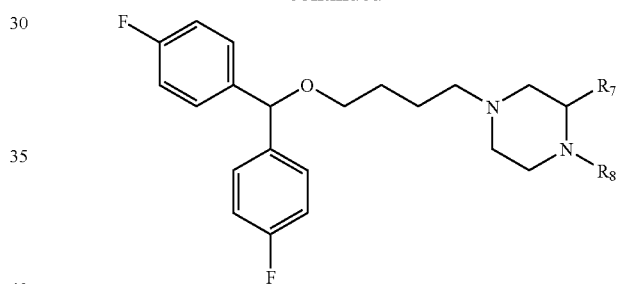

27 R₇ = =O, R₈ = H
28 R₇ = Ph, R₈ = H
29 R₇ = H, R₈ = Ph
30 R₇ = H, R₈ = 2-F-Ph
31 R₇ = H, R₈ = 4-F-Ph
32 R₇ = H, R₈ = 2-Cl-Ph
33 R₇ = H, R₈ = 3-Cl-Ph
34 R₇ = H, R₈ = 4-Cl-Ph
35 R₇ = H, R₈ = 2-OCH₃-Ph
36 R₇ = H, R₈ = 4-NO₂-Ph
37 R₇ = H, R₈ = 4-CH₃CO-Ph
38 R₇ = H, R₈ = 4-NO₂-Ph
39 R₇ = H, R₈ = 2-pyridyl
40 R₇ = H, R₈ = COPh
41 R₇ = H, R₈ = piperonyl
42 R₇ = H, R₈ = SO₂-4—NO₂-Ph 3 →(benzoyl chloride, K₂CO₃/KI)→

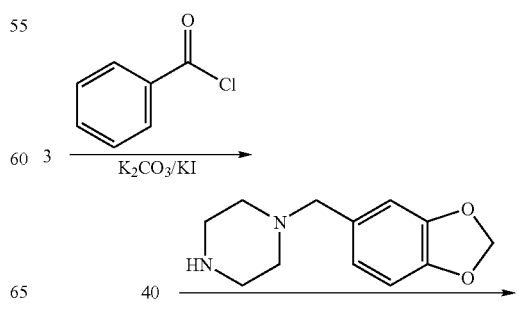

40 →(amine, K₂CO₃/KI)→

-continued

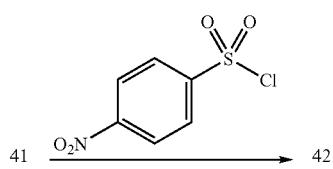

The preferred compounds are

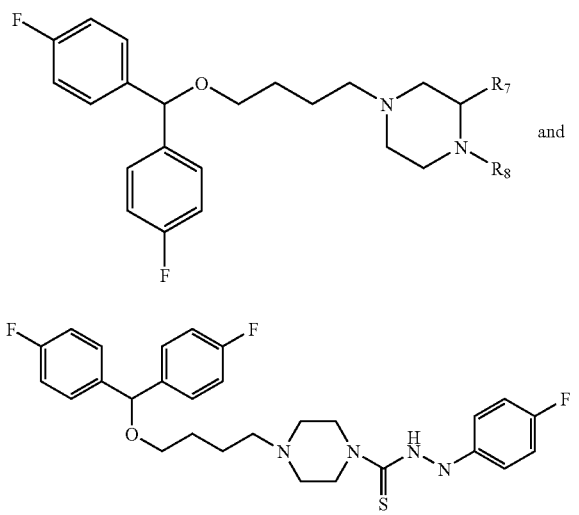

Example I

The synthetic scheme for the preparation of representative bisarylmethoxyalkylpiperazine compounds of this invention is depicted in Scheme 1. Compound 2 was made by reacting 6.5 g of 4-chloropropanol with 2.2 g of 4,4'-difluorobenzhydrol in toluene, in the presence of concentrated sulfuric acid for 6 hours at reflux temperature. The reaction mixture was cooled, washed with a saturated solution of $NaHCO_3$ and $H_2O$. The organic layer was dried over magnesium sulfate, filtered and the volatiles were evaporated. The resultant colorless oil was applied for column separation on silica gel. Elution with 3% ethyl acetate/hexane afforded 2.3 g of product as a colorless oil.

Compound 3 was prepared from compounds utilizing piperazine (25 g) as a reagent dissolved in 100 ml of DMF and stirred with 8 g of compound 2 for 48 hours. Compound 3 was purified by column chromatography (silica gel) and then dissolved in methylene chloride. To this solution, one of the isocyanates listed in Scheme 1 was added. The reaction mixture was stirred for 24 hours at room temperature. The products 4, 5, 6, 7 or 8 (Table 1) were isolated in 80-85% yield.

Referring to Scheme 2, compound 9 is obtained by reacting compound 2 with nipecotamide. Compound 9 was isolated in 90% yield. Compound 9 then is reacted with lithium aluminum hydride to give compound 10 as a yellow oil. Compound 10 then is reacted with m-$CF_3$-PhCOCl and triethylamine in methylene chloride to produce compound 11 (Table 2). Alternatively, compound 10 is reacted either with p-fluorophenyl isocynate to produce compound 12 or with p-fluorobenzyl-isocyanate to produce compound 13 (Table 2) under the same conditions used for compounds 5-8.

Referring to Scheme 3, compound 14 is treated with ether 4-fluorophenyl isocyanate, 4-fluorobenzyle isocyante or m-C $F_3$-PhCOCl under the same conditions used to produce compounds 4-6 and 11 to produce compound 15. Compound 15 is then heated at reflux for 48 hours with KOH in methanol to produce compound 16 after silica gel chromatography. Compound 16 then is treated with compound 2 under the same conditions used to produce compound 3.

Referring to Scheme 4, compound 2 is reacted with 4-cyano-4-phenyl piperidine HCl to produce compound 20 under the same conditions used for compound 3. Compound 20 is heated with lithium aluminum hydride for 24 hours to produce compound 21. Compound 21 then is treated with either p-fluorophenyl isocynanate to produce compound 22, acetyl chloride, p-fluorophenyl sulfonyl chloride, 3-maleimidopropionic acid or chloroacetyl chloride to produce compounds 22. 23. 24. 25 or 26 (Table 4) under the same conditions. used for compounds 4-8 and 11-13. For compound 25, amine 21 was treated with 3-maleimidopropionic acid, DCC and 1-hydroxybentriazole in DMF.

The products were characterized by IR, NMR and elemental analysis and were consistent with the structures shown in Schemes 1-4. The products were converted to salts, either oxalate or hydrochloride and evaluated for their ability to inhibit the neurotransmitter (dopamine-DA, norepinephrine-NE, and serotonin-5-HIT) reuptake systems. The evaluation method used was as follows:

Drugs (10 mM stock solution) are dissolved in DMSO. The final DMSO concentration in the assay is 0.01 percent. Pipetting is performed with a Biomek 2000 robotic workstation. [$I^{125}$] RTI-55 Binding:

Preparation Cells are grown on 150 mm diameter tissue culture dishes. Medium is poured off the plate, the plate is washed with 10 ml of phosphate buffered saline, and 10 ml of lysis buffer (2 mM HEPES, 1 mM EDTA) are added. After 10 min, cells are scraped from plates and poured into centrifuge tubes and centrifuged for 20 min at 30,000×g. Supernatant is removed, and the pellet is resuspended in 20-32 ml 0.32 M sucrose, depending on the density of binding sites in a given cell line (i.e., a resuspension volume which results in binding ≦10% of the total radioactivity), with a Polytron at setting 7 for 10 sec.

Assay: Each assay contains 50 μL of [ISuprscpt 125] RTI-55 (40-80 pM final concentration) in a final volume of 250 μl. Krebs HEPES is used for all assays. Membranes are preincubated for 90 min. At room temperature in the dark and is terminated by filtration onto GF/C filters using a Tom-tech harvester. Scintillation fluid is added to each square and radioactivity remaining on the filter is determined using a Wallac μ- or β-plate reader. Competition experiments are conducted with duplicate determinations. Data is analyzed using GraphPAD Prism, with $IC_{50}$ values converted to $K_1$ values using the Cheng-Prusoff equation.

[³H] Neurotransmitter Uptake for 11EK 293 Cells Expressing Recombinant Amine Transporters: Filtration Assay Preparation: Cells are plated on 150 mm dishes and grown until confluent. The medium is removed, and cells are washed twice with room temperature phosphate buffered saline (PBS). Following addition of PBS (3 ml), the plates are placed in a 25° C. water bath for 5 min. The cells are gently scraped then triturated with a pipette. Cells from multiple plates are combined. One plate provides enough cells for 48 wells, which test two drug curves.

Assay: The assay is conducted in 96 1 ml vials and uses the Tomtech Harvester and Betaplate reader. Krebs HEPES (350 μl) are added to vials and placed in a 25° C. water bath. Cells (50 μl) are added, preincubated for 10 min. and [³H]DA, [³H]5HT or [³H]NE (50 μl, 20 nM final concentration) is added. Uptake is terminated after 10 min. By filtration on the Tomtech Harvester using filters presoaked in 0.05% polyethylenimine. Assays are conducted in triplicate with 6 drug concentrations. Data is analyzed using GraphPAD Prism.

In Vitro Biological Results.

The results obtained with the binding and inhibition tests are shown in Tables 1 and 1-1. The units of measure for the values shown in Tables 1 and 1.1 are in nM (nanomolar).

The results in Table 1 and 1-1 show that most of the new compounds demonstrate the ability to inhibit dopamine uptake at concentrations comparable to or lower than that reported for cocaine. The IC$_{50}$ values approach those cited for the potent inhibitors GBR12909 and GBR12935. The biphenylurea derivative 8_ which possessed the highest affinity, also demonstrated high selectivity for the dopamine transporter (67 nM) as compared to norepinephrine (6940 nM) or serotonin (>10,000 nM transporter).

TABLE 1

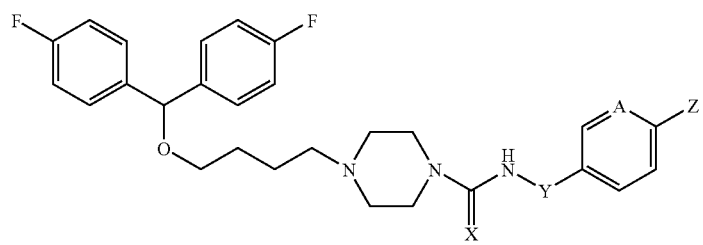

Binding Affinities and Selectives of Bisarylmethoxybutylpiperazine derivatives at the DA, 5-HT and NE Transporters Labeled with [$^{125}$] IRTI-55 (Ki ± SD, nM)$^a$

| Compound | X | Y | A | Z | DAT | SERT | NET | SERT/DAT | NET/DAT |
|---|---|---|---|---|---|---|---|---|---|
| | | | | | | Binding Ratios | | | |
| 4 | O | | | F | 60 ± 8 | 14 ± 6 | 133 ± 18 | 0.2 | 2.2 |
| 5 | O | CH$_2$ | | F | 437 ± 12 | 275 ± 21 | 706 ± 153 | 0.2 | 1.6 |
| 6 | S | | N | | 170 ± 24 | 1080 ± 300 | 2450 ± 367 | 6.4 | 14.4 |
| 7 | O | SO$_2$ | | F | 334 ± 25 | 3160 ± 666 | 2690 ± 258 | 9.5 | 8.1 |
| 8 | O | | | pH | 67 ± 11 | >10 μM | 6940 ± 702 | >149 | 104 |
| Cocaine | | | | | | 515 ± 27 | 530 ± 62 | 2820 ± 168 | |

Results are average ± SEM of three independent experiments assayed in triplicate.

TABLE 1-1

DA, 5-HT and NE Reuptake Inhibition and Ratios of Reuptake to binding of Bisarylmethoxybutylpiperazine derivatives at the DA Transporters (IC$_{50}$ ± SD, nM)$^a$

| | Reuptake Inhibition (IC$_{50}$ ± SD, nM)$^a$ | | | Discrimination Ratios [³H]DA reuptake/ |
|---|---|---|---|---|
| Compound | [³H]DA | [³H]5-HT | [³H]NE | DAT binding |
| 4 | 9 ± 3 | 68 ± 28 | 45 ± 17 | 0.2 |
| 5 | 53 ± 22 | 6 ± 1 | 51 ± 4 | 0.1 |
| 6 | 97 ± 19 | 308 ± 102 | 359 ± 108 | 0.6 |
| 7 | 206 ± 64 | 1620 ± 769 | 836 ± 93 | 0.6 |
| 8 | 419 ± 34 | 1020 ± 320 | 56.3 ± 9.4 | 6.3 |
| Cocaine | 278 ± 53 | 1990 ± 316 | 754 ± 189 | |

Results are average ± SEM of three independent experiments assayed in triplicate.

Example II

The filtrate assay and assays was conducted in the same manner as in Example I. The results obtained with binding and inhibition tests are shown in Tables 2 and 2.1. The units of measure for the values shown in Table 2 and 2.1 are in nM (Nanomolar).

TABLE 2

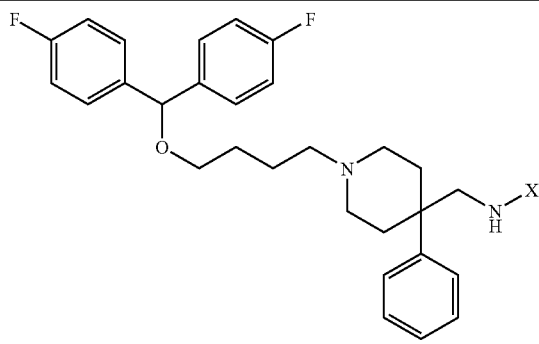

Binding Affinities and Selectivities of Bisarylmethoxybutylpiperazine derivatives at the DA, 5-HT and NE Transporters Labeled with [$^{125}$I] RTI-55 (Ki ± SD. NM)$^a$

|          |        |        | Binding Ratios |          |          |          |         |
|----------|--------|--------|----------------|----------|----------|----------|---------|
| Compound | X      | Y      | DAT            | SERT     | NET      | SERT/DAT | NET/DAT |
| 10       |        |        | 113 ± 8        | 883 ± 32 | 537 ± 112| 7.8      | 4.8     |
| 11       |        | 3-CF$_3$ | 403 ± 81    | 496 ± 177| 49 ± 21  | 1.2      | 0.1     |
| 12       | NH     | 4-F    | 93 ± 38        | 198 ± 35 | 99 ± 40  | 2.1      | 1.1     |
| 13       | NHCH$_2$ | 4-F  | 203 ± 68       | 545 ± 194| 60 ± 15  | 2.7      | 0.3     |
| Cocaine  |        |        | 120 ± 38       | 138 ± 48 | 243 ± 25 |          |         |

Results are average ± SEM of three independent experiments assayed in triplicate.

TABLE 2-1

DA, 5-HT and NE Reuptake Inhibition and Ratios of Reuptake to binding of Bisarylmethoxybutylpiperazine derivatives at the DA Transporters (IC$_{50}$ ± SD, nM)$^a$

|          | Reuptake Inhibition (IC$_{50}$ ± SD, nM) | | | Discrimination Ratios [$^3$H]DA reuptake/ |
|----------|--------|---------|---------|---------|
| Compound | [$^3$H]DA | [$^3$H]5-HT | [$^3$H]NE | DAT binding |
| 10       | 31 ± 9  | 571 ± 127 | 118 ± 6  | 0.3 |
| 11       | 46 ± 12 | 511 ± 201 | 53 ± 3   | 0.1 |
| 12       | 92 ± 24 | 123 ± 16  | 20 ± 5   | 1.0 |
| 13       | 85 ± 39 | 177 ± 18  | 136 ± 32 | 0.4 |
| Cocaine  | 207 ± 63| 277 ± 48  | 286 ± 28 |     |

Results are average ± SEM of three independent experiments assayed in triplicate.

Compounds 10-13 were tested for its effects on radioligand [I$^{125}$] RTI-55)_binding to and [$^3$H] dopamine uptake by HEK cells expressing cDNA for the human dopamine transporter (HEK-hDAT cells), its effect on radioligand ([I$^{125}$] RTI-55) binding and [$^3$H] serotonin uptake by HEK cells expressing cDNA for the human serotonin transporter (HEK-hSERT cells), and its effects on radioligand ([I$^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was lower or similar to the affinity of cocaine, the standard compound, for the same site(s). The K$_i$ value for the displacement of [I$^{125}$] RTI-55 by compound 12 was 93 nM, and the K$_i$ value for cocaine displacement of [I$^{125}$] RTI-55 binding was 120 nM. In the uptake assays compound 10 had higher potency at blocking the uptake of [$^3$H] dopamine, with an IC$_{50}$ value of 31 nM, as compared to the potency of cocaine (IC$_{50}$=207 nM).

In BEK-hSERT cells, the affinity of the compound for the binding site was lower than the affinity of cocaine, the standard compound, for the same site(s). The K$_1$ value for the displacement of [I$^{125}$] RTI-55 by compound 12 was 198 nM, and the K$_1$ value for cocaine displacement of [I$^{125}$] RTI-55 binding was 138 nM. In the uptake assays, compound 10 was less potent at blocking the uptake of [$^3$H] serotonin, with an IC$_{50}$ value of 883 nM, as compared to the potency of cocaine (IC$_{50}$=277 nM).

In HEK-hNET cells, the affinity of the compound for the binding site was higher than the affinity of cocaine, the standard compound, for the same site(s). The K$_1$ value for the displacement of [I$^{125}$] RTI-55 by compound 12 was 99 nM, and the K$_1$ value for cocaine displacement of [I$^{125}$] RTI-55 binding was 243 nM. In the uptake assays, compound 10 was less potent at blocking the uptake of [$^3$H] norepinephrine, with an IC$_{50}$ value of 537 nM, as compared to the potency of cocaine (IC$_{50}$=286 nM).

In BEK-hDAT cells, the affinity of compound 10 for the binding site was higher than the affinity of cocaine, the standard compound, for the same site(s). The K$_i$ value for the displacement of [I$^{125}$] RTI-55 by 10 was 113 nM, and the K$_i$ value for cocaine displacement of [I$^{125}$] RTI-55 binding was 120 nM. In the uptake assays, compound 11 was more potent at blocking the uptake of [$^3$H] dopamine, with an IC$_{50}$ value of 46 nM, as compared to the potency of cocaine (IC$_{50}$=207 nM).

In BEK-hSERT cells, the affinity of the compound 10 for the binding site was lower than the affinity of cocaine, the standard compound, for the same site(s). The K$_1$ value for the displacement of [I$^{125}$] RTI-55 by 10 was 883 nM, and the K$_1$ value for cocaine displacement of [I$^{125}$] RTI-55 binding was 138 nM. In the uptake assays, 11 was less potent at blocking the uptake of [$^3$H] serotonin, with an IC$_{50}$ value of 511 nM, as compared to the potency of cocaine (IC$_{50}$=277 nM).

In HEK-hNET cells, the affinity of the compound for the binding site was higher than the affinity of cocaine, the standard compound, for the same site(s). The $K_1$ value for the displacement of $[I^{125}]$ RTI-55 by compound 13 was 60 nM, and the $K_1$ value for cocaine displacement of $[I^{125}]$ RTI-55 binding was 243 nM. In the uptake assays, Compound 12 was more potent at blocking the uptake of $[^3H]$ norepinephrine, with an $IC_{50}$ value of 20 nM, as compared to the potency of cocaine ($IC_{50}$=286 nM).

Example III

The filtrate assay and assays was conducted in the same manner as in Example I. The results obtained with binding and inhibition tests are shown in Tables 3 and 3.1. The units of measure for the values shown in Table 3 and 3.1 are in nM (Nanomolar).

TABLE 3

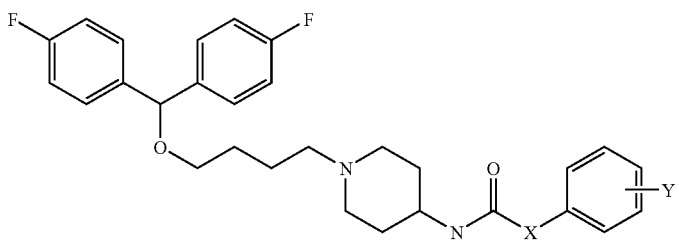

Binding Affinities and Selectivities of Bisarylmethoxybutylpiperazine derivatives at the DA, 5-HT and NE Transporters Labeled with $[^{125}I]$ RTI-55 (Ki ± SD. NM)$^a$

| | | | Binding Ratios | | | | |
|---|---|---|---|---|---|---|---|
| Compound | X | Y | DAT | SERT | NET | SERT/DAT | NET/DAT |
| 17 | NH | 4-F | 32 ± 1.4 | 279 ± 57 | 430 ± 100 | 8.7 | 13.4 |
| 18 | NHCH$_2$ | 4-F | 1.7 ± 0.3 | 206 ± 37 | 43 ± 16 | 121 | 25.3 |
| 19 | | 3-F | 9 ± 1 | 118 ± 15 | 266 ± 79 | 13.1 | 29.6 |
| Cocaine | | | 522 ± 24 | 529 ± 31 | 151 ± 41 | | |

Results are average ± SEM of three independent experiments assayed in triplicate.

TABLE 3-1

DA, 5-HT and NE Reuptake Inhibition and Ratios of Reuptake to binding of Bisarylmethoxybutylpiperazine derivatives at the DA Transporters ($IC_{50}$ ± SD, nM)$^a$

| | Reuptake Inhibition ($IC_{50}$ ± SD, nM) | | | Discrimination Ratios [$^3$H]DA reuptake/ |
|---|---|---|---|---|
| Compound | [$^3$H]DA | [$^3$H]5-HT | [$^3$H]NE | DAT binding |
| 17 | 7000 ± 1790 | 7140 ± 3360 | 2530 ± 61 | 219 |
| 18 | 1050 ± 291 | >10 μM | 1670 ± 688 | 618 |
| 19 | 6080 ± 1090 | >10 μM | >10 μM | 676 |
| Cocaine | 483 ± 45 | 518 ± 22 | 328 ± 176 | |

Results are average ± SEM of three independent experiments assayed in triplicate.

Compounds 17-19 was tested for its effects on radioligand $I^{125}]$ RTI-55) binding to and [$^3$H] dopamine uptake by HEK cells expressing cDNA for the human dopamine transporter (HEK-hDAT cells), its effect on radioligand ($[I^{125}]$ RTI-55) binding and [$^3$H] serotonin uptake by HEK cells expressing cDNA for the human serotonin transporter (HEK-hSERT cells), and its effects on radioligand ($[I^{125}]$ RTI-55) binding and [$^3$H] norepinephrine uptake by HEK cells expressing cDNA for the human norepinephrine transporter (HBEK-hNET cells).

In HEK-hDAT cells, the affinity of the compound for the binding site was higher than the affinity of cocaine, the standard compound, for the same site(s). The $K_i$ value for the displacement of $[I^{125}]$ RTI-55 by 18 was 1.7 nM, and the $K_i$ value for cocaine displacement of $[I^{125}]$ RTI-55 binding was 522 nM. In the uptake assays, 18 was less potent at blocking the uptake of [$^3$H] dopamine, with an $IC_{50}$ value of 1670 nM, as compared to the potency of cocaine ($IC_{50}$=328 nM).

In BEK-hSERT cells, the affinity of the compound for the binding site was about the same as the affinity of cocaine, the standard compound, for the same site(s). The $K_1$ value for the displacement of $[I^{125}]$ RTI-55 by 19 was 118 nM, and the $K_1$ value for cocaine displacement of $[I^{125}]$ RTI-55 binding was 529 nM. In the uptake assays, 17 was less potent at blocking the uptake of [$^3$H] serotonin, with an $IC_{50}$ value of 7140 nM, as compared to the potency of cocaine ($IC_{50}$=518 nM).

In HEK-hNET cells, the affinity of the compound for the binding site was higher than the affinity of cocaine, the standard compound, for the same site(s). The $K_1$ value for the displacement of $[I^{125}]$ RTI-55 by 18 was 43 nM, and the $K_1$ value for cocaine displacement of $[I^{125}]$ RTI-55 binding was 151 nM. In the uptake assays, 17 had about the less potency at blocking the uptake of [$^3$H] norepinephrine, with an $IC_{50}$ value of 2530 nM, as compared to the potency of cocaine ($IC_{50}$=328 nM).

Example IV

The filtrate assay and assays was conducted in the same manner as in Example I. The results obtained with binding and inhibition tests are shown in Tables 4 and 4.1. The units of measure for the values shown in Table 4 and 4.1 are in nM (Nanomolar).

TABLE 4

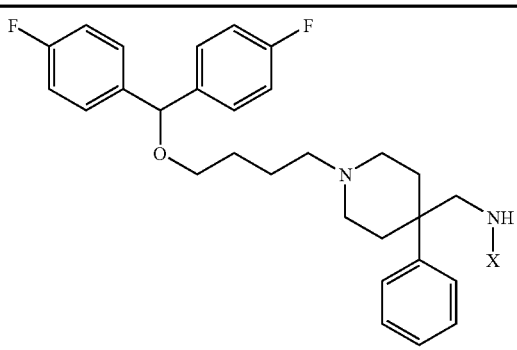

Binding Affinities and Selectivities of Bisarylmethoxybutylpiperazine derivatives at the DA. 5-HT and NE Transporters Labeled with [$^{125}$I] RTI-55 (Ki ± SD. NM)$^a$

| Compound | X | DAT | SERT | Binding Ratios SERT/DAT |
|---|---|---|---|---|
| 21 | H | 140 ± 53 | 347 ± 152 | 2.5 |
| 22 | —CONH(4F-pH) | 83 ± 33 | 234 ± 63 | 2.8 |
| 23 | —COCH$_3$ | 172 ± 14 | 258 ± 76 | 1.5 |
| 24 | —SO$_2$(4Cl-Ph) | 451 ± 18 | 533 ± 129 | 1.2 |
| 25 | —COCH$_2$CH$_2$, Maleimide | 827 ± 197 | 6400 ± 2680 | 7.7 |
| 26 | —COCH$_3$Cl | 316 ± 77 | 580 ± 177 | 1.8 |
| Cocaine | | 504 ± 54 | 268 ± 43 | |

Results are average ± SEM of three independent experiments assayed in triplicate.

TABLE 4-1

DA, 5-HT and NE Reuptake Inhibition and Ratios of Reuptake to binding of Bisarylmethoxybutylpiperazine derivatives at the DA Transporters (IC$_{50}$ ± SD, nM)$^a$

| Compound | Reuptake Inhibition (IC$_{50}$ ± SD, nM) [$^3$H]DA | [$^3$H]5-HT | Discrimination Ratios [$^3$H]DA reuptake/ DAT binding |
|---|---|---|---|
| 21 | 155 ± 37 | 337 ± 128 | 1.1 |
| 22 | >10 µM | 367 ± 62 | 120.5 |
| 23 | 129 ± 32 | 359 ± 78 | 0.8 |
| 24 | >10 µM | 4580 ± 1180 | 22.2 |
| 25 | 988 ± 305 | 3120 ± 1470 | 1.2 |
| 26 | 486 ± 250 | 270 ± 78 | 1.5 |
| Cocaine | 243 ± 43 | 238 ± 71 | |

Results are average ± SEM of three independent experiments assayed in triplicate. Compounds 21-26 was tested for its effects on radioligand [$^{125}$I] RTI-55)_binding to and [$^3$H] dopamine uptake by HEK cells expressing cDNA for the human dopamine transporter (HEK-hDAT cells), its effect on radioligand ([I$^{125}$] RTI-55) binding and [$^3$H] serotonin uptake by HEK cells expressing cDNA for the human serotonin transporter (HEK-hSERT cells), and its effects on radioligand ([I$^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was higher than the affinity of cocaine, the standard compound, for the same site(s). The K$_i$ value for the displacement of [I$^{125}$] RTI-55 by 22 was 83 nM, and the K$_i$ value for cocaine displacement of [I$^{125}$] RTI-55 binding was 504 nM. In the uptake assays, 21 had about the same potency at blocking the uptake of [$^3$H] dopamine, with an IC$_{50}$ value of 155 nM, as compared to the potency of cocaine (IC$_{50}$=243 nM In HEK-hSERT cells, the affinity of the compound for the binding site was similar or lower than the affinity of cocaine, the standard compound, for the same site(s). The K$_i$ value for the displacement of [I$^{125}$] RTI-55 by 22 was 234 nM, and the K$_i$ value for cocaine displacement of [I$^{125}$] RTI-55 binding was 268 nM. In the uptake assays, 26 was less potent at blocking the uptake of [$^3$H] serotonin, with an IC$_{50}$ value of 270 nM, as compared to the potency of cocaine (IC$_{50}$=238 nM).

Example V

Chemistry

The synthetic scheme for the preparation of hybrid bisarylmethoxybutylpiperate analogs is depicted in Scheme 5. The requisite starting materials 1,$^{22}$ (Bioorg. Med. Chem. Lett. 1997, 7, 2559-2564), 2-phenylpiperazine$^{27}$ (J. Am. Chem. Soc. 1940, 62, 1202-1204) and 2-ketopiperazine (J. Am. Chem. Soc. 1996, 9, 181-185) were prepared essentially according to literature procedures with or without slight modifications. The N-alkylated target compounds were prepared by alkylation of the appropriate amine with alkylating agent such as [bis(4-fluorophenyl)methoxy]butyl chloride 2 in the presence of K$_2$CO$_3$ as base and KI as catalyst in good yields (83-87%). The final products were converted in oxalate salts for the elemental analysis and biological evaluation.

In vitro Biological Results: This Example was designed to develop new agents with higher DAT affinity and weak potency of DA reuptake by selective modifications of the substituents on a piperidine ring template (Bisarylmethoxyalkylpiperidines, FIG. 1). Also to find new lead compound(s) as potential cocaine antagonists, new moieties for hydrogen bonding and aromatic function were introduced. Such modifications were presumed to be a critical structural determinant for dual activity at DAT and DA/5-HT receptor sites. These efforts led to the preparation and characterization of a new series of (bisarylmethoxy)butylpiperazine analogs. For the evaluation of their biological properties, the final products were converted into oxalate salt forms.

Neurotransmitter Activities. The analogs were evaluated for their ability to displace [$^{125}$I]RTI-55 (a cocaine analog, binding affinity) as well as for potency of reuptake inhibition (IC$_{50}$) of DA, 5-HT and NE with HEK 293 cells expressing cDNA for human dopamine transporter (hDAT), human serotonin transporter (hSERT) or human norepinephrine transporter (hNET). The results of these studies are shown in Tables 5 and 6.

As shown in Table 6, most of the new bisarylbutoxypiperazine compounds inhibited DA reuptake at concentrations (301-4200 nM, IC$_{50}$) comparable to or lower than that reported for cocaine (237-393 nM, IC$_{50}$). Although the substituted arylpiperazines can be considered to be derivatives of serotonergic agents, these agents demonstrated strong to moderate affinity at the DAT (3.8-760 nM) and wide range of DR values (0.6 to 144). Apparently the presence and location of certain substituent group(s) modulated binding selectivity weakly but severely for DR values (potency of DA reuptake). Transposition of aromatic group from 4- to 3-position (29 vs. 28) of the piperazine ring resulted in a dramatic increase in both potency of binding, its selectivity and a DR value of 144. Substitution of aromatic ring with ketone (28 to 27) resulted in loss of activities (DR≈1).

DA/5-HT Receptor Activities. Compounds 28, 29, 34, 35, 39, and 40 were evaluated for their ability to bind and function at DA and 5-HT receptor sites; based on the facts that arylpiperazines are the basic pharmacophore for the activity at DA and 5-HT receptor sites. The potency and selectivity of the selected target compounds for DA and 5-HT receptors were evaluated using ligand displacement assays (see Table 7 for radioligands and cell types used). $D_2$ and $D_3$ antagonistic activities were assessed in vitro by the ability of the compounds to block [$^3$H]thymidine incorporation (inhibition of mitogenesis) induced by 10 nM quinpirole in $CHO_p$-$D_2$ and $D_3$ cells. The results of the in vitro pharmacologic testing are found in Table 7. All compounds evaluated had weak to moderate affinity and antagonistic activity at $D_3$ and/or $D_2$ sites except compound 34 which showed selective and strong antagonistic activity at $D_3$ site. As expected, bulky bisaryl group was not well tolerated in terms of DA activities. Substituted arylpiperazines are commonly present in serotonergic agents; most analogs didn't have activity at those sites (moderate binding for 35 and 39 for $5\text{-HT}_{1A}$). 4-Chloro-arylpiperazine 34 showed selective and potent antagonistic activities at $D_3$ receptor. Based on the results of these functional assays; these analogs are not full antagonists and less severe extrapyramidal side-effects than conventional DA antagonists might be expected.

In Vivo Locomotor Activity: Based on their in vitro activities at the DAT (selectivity also) and DR values, compounds 28, 39 (high DR) and 30, 36 and 42 (low DR) were selected for preliminary behavioral screening which involved testing alone and in combination with cocaine for effect on locomotor activity (LMA) in mice. Likewise, the effects of the dopaminergic antagonists (28 and 39) on cocaine-induced hyperactivity were studied. As summarized in Table 8, compound 28 and 30 produced a significant increase on spontaneous LMA with low $EC_{50}$ compared to GBR 12909. Significant suppression of spontaneous LMA was demonstrated only by compound 36 with $ID_{50}$ of 113 mg/kg. Compound 28 and 39 produced a dose-dependent biphasic effect on LMA in 8 hour time course studies. Biphasic effects on spontaneous LMA by $D_2$/$D_3$ dopaminergic antagonistic ligands have been previously demonstrated with other compounds. Since these ligands possess activities at the DAT and are moderate affinity inhibitors of DA reuptake their effects on LMA are probably the result of activities at both DAT and DA receptor sites. Maximal stimulatory effects on spontaneous LMA by 28 and 30 were only 30 to 50% of that achieved with cocaine as shown by the ratio of ME/CME in Table 8. Attenuation of cocaine-induced LMA (20 mg/kg of cocaine) was demonstrated by compound 28, 35 and 39. But compound 30 and 42 failed to attenuate the hyperlocomotion induced by cocaine. Correlations between DR values and $EC_{50}$ and $AD_{50}$ were not detected, however, other factors such as potency as $D_2$/$D_3$ antagonists and pharmacokinetic factors (uptake rate into brain) might be critical factors for the potency in LMA studies.

CONCLUSIONS

The change of piperidine to piperazine ring resulted in retention of transporter affinity and DA reuptake inhibition. Such modification resulted in DA receptor affinity and selectivity (when compared with 5-HT receptors). These results provided interesting insights about possible structural similarities between ligands binding sites on the DAT and DA receptors. This example provides additional information on pharmacophores which are responsible for selective binding and potency of reuptake inhibition at the DAT and on activities at the DA/5-HT receptor sites. Even though the correlations between in vitro DR values and in vitro potency in LMA activities were not observed, these new analogs along with the results of the LMA studies provide a basis for the design of other ligands with strong binding to the DAT, low potency inhibition DA reuptake and binding to DA/5-HT receptor sites.

General Experimental Methods. Melting points were determined with a Thomas-Hoover melting point apparatus and were uncorrected Elemental analyses were performed by Atlantic Microlabs, Atlanta, Ga., and were within 0.4% of theory unless noted otherwise. $^1$H NMR spectra were recorded with a Varian XL-500 spectrometer. Chemical shifts are expressed in parts per million (ppm) on the δ scale relative to a TMS internal reference standard. In general, $CDCl_3$ was used for the free bases and DMSO-$d_6$ was used for salts. Coupling constants (J values) were given in Hz. Thin layer chromatography (TLC) was performed on 250 µm thickness silica gel plates or alumina precoated plates (Whatman, A L SIL G/UV or J. T. Baker, Baker-flex, SILICA GEL IB-F) containing fluorescent indicator (2×8 cm). Column chromatography was performed on silica gel (Baker, 40 µm Flash chromatography). Fractions were analyzed using TLC and compounds were visualized using ninhydrin (0.5 g in 100 mL of methanol) for primary and secondary amine(s), ultraviolet light and/or iodine vapor. Free bases were dissolved in ethyl acetate and/or diethyl ether, filtered and precipitated by addition of a solution of oxalic acid. The resulting solids were collected by filtration and recrystallized.

Synthetic Chemical Methods.

2-Oxo-piperazine: A solution of ethyl chloroacetate (4.9 g, 40 mmol) in 40 mL of absolute ethanol was slowly added dropwise over a period of 3.5 h at ambient temperature to ethylenediamine (24 g, 400 mmol) in 100 mL of absolute ethanol. The reaction mixture was allowed to stand for 2 h after addition was completed. Sodium ethoxide (15 mL, 40 mmol, 21 wt. % solution in denatured ethylalcohol) was added. The precipitated sodium chloride was filtered off, the solvent was removed by evaporation and 40 mL of DMF was added to the resultant red oil. The reaction mixture was allowed to stir for 24 h at ambient temperature and then heated at about 60° to 70° C. while removing the volatile materials with $N_2$ gas. The resultant yellow solid was applied to silica gel column for separation. The crude product (3.3 g, 33 mmol, 82%) was obtained by elution with a solvent mixture ($CHCl_3$:MeOH:$NH_4OH$/9:1:0.1). This crude yellow solid was used for next synthesis without further purification. Recrystalization three times from acetone gave well-defined, pure-white crystals. $^1$H NMR ($CDCl_3$): δ 1.70 (1H, br s), 3.03 (2H, t, J=5.4), 3.37 (2H, td, J=2.3, 5.4), 3.52 (2H, s), 6.54 (1H, br s). $^{13}$C NMR ($CDCl_3$): δ 42.31, 43.05, 49.83, 170.00. mp: 132°-134° (uncorr.) [lit.] mp:136° (corr.) (American Chemical Society Journal, 62 (1940) 1202-1204.)

2-oxo-3-phenyl-piperazine: To a solution of α-bromophenylacetic acid (2.15 g, 10 mmol) in ethanol (30 mL) was added 1M HCl in ether (5 mL) and the solution was heated under reflux overnight. The reaction mixture was concentrated to a brown oil (ethyl α-bromophenylacetate), which was used without further purification. A solution of crude ethyl α-bromophenylacetate (2.43 g, 10 mmol) in ethanol (20 mL) was added dropwise to a stirred solution of ethylenediamine (1.2 g, 20 mmol) in 30 mL of ethanol. After the addition was completed, a solution of sodium ethoxide (8.5 mL, 20 mmol, 21 wt. % solution in ethyl alcohol) was added and the reaction was heated under reflux 16 h. The excess ethylenediamine and ethanol were removed under reduced pressure. The residue was extracted with ethyl acetate (200 mL×3), washed with saturated NaCl solution (30 mL×2), dried over $MgSO_4$ and filtered. The crude yellow solid obtained by rotary evaporation of ethyl acetate was purified by silica gel column chromatography. The white solid (1.1 g, 6.2 mmol, 62%) was obtained by elution with $CHCl_3$:MeOH:$NH_4OH$ (9:1:0.1). $^1$H NMR (DMSO-$d_6$): δ 2.75-2.95 (2H, m), 2.95

(1H, br s), 3.10-3.15 (1H, m), 3.21-3.25 (1H, m), 4.29 (1H, s), 7.20-7.37 (5H, m), 7.78 (1H, s). mp: 138°-140° (uncorr.) [lit.] mp: 139°-139.5° (corr.)

2-phenyl-piperazine. 2-Oxo-3-phenyl-piperazine (1.76 g, 10 mmol), in 30 mL of anhydrous THF was added dropwise to a 20 mL (20 mmol) of 1M solution of LiAH$_4$ in THF, and the mixture was stirred at room temperature for 24 h. After workup (water, 20% NaOH addition to destroy excess LiAH$_4$), the mixture was filtered and the filter cake was reextracted with ethyl acetate. The combined organic filtrate and exam were dried over MgSO$_4$, filtered and evaporated to give an slightly yellow solid that was purified by silica gel column chromatography (CHCl$_3$:MeOH:NH$_4$OH/9:1:0.1). The reduced product was isolated as a colorless solid (960 mg, 6 mmol, 60%). $^1$H NMR (CDCl$_3$): δ 2.69 (1H, t, J=11.3), 2.85-3.10 (7H, m), 3.76 (1H, br d, J=8.9), 7.21-7.38 (5H, m). mp (free base): 79°-81° C.

1-[Bis(4-fluorophenyl)methoxy]-4-chlorobutane (2). A mixture of 4-chloro-1-butanol (6.51 g, 60 mmol), 1 mL of concentrated sulfuric acid and 4,4'-difluorobenzhydrol (2.2 g, 10 mmol) in 50 mL of toluene was heated at reflux for 12 h. The reaction mixture was cooled, washed successively with saturated sodium bicarbonate solution (50 mL) and water (50 mL). The organic layer was dried over MgSO$_4$, filtered and the solvent was removed by rotary evaporation. The resultant brown oil was purified on a silica gel column. Elution with 2% ethyl acetate/hexane afforded 2.33 g (7.5 mmol, 75%) of the product as a colorless oil. $^1$H NMR (CDCl$_3$): δ 1.71-1.80 (2H, m), 1.84-1.93 (2H, m), 3.43 (2H, t, J=6.0), 3.52 (2H, t, J=6.4), 5.30 (1H, s) 6.95-7.02 (4H, m), 7.24-7.29 (4H, m)

1-[1-[bis(4-florophenyl)methoxy]butyl]piperazine (3). Piperazine (4.31 g, 50 mmol) was dissolved in 40 mL of anhydrous DMF and stirred with K$_2$CO$_3$ powder (2.76 g, 20 mmol) and KI (100 mg, 0.6 mmol) for 0.5 h. To this turbid solution, 1-[bis(4-fluorophenyl)methoxy]-4-chlorobutane (2, 1.55 g, 5 mmol) in 10 mL of DMF was added slowly. The reaction mixture was stirred for 72 h at 60°-70°. The turbid reaction Ore was poured into 200 mL of ethyl acetate, washed with sat NaCl solution (60 mL×5), dried over MgSO$_4$ and evaporated to dryness. The crude oil was applied to a silica gel column for purification. Elution with CHCl$_3$:MeOH (93:7) afforded the desired mono-alkylated product 3 (540 mg, 1.5 mmol, 30%) as a slightly yellow oil. $^1$H NMR (CDCl$_3$): δ 1.55-1.69 (4H, m), 2.31 (2H, t, J=7.5), 2.39 (4H, br s), 2.88 (4H, t, J=4.8), 3.43 (2H, t, J=6.0), 5.28 (1H, s), 6.98-7.02 (4H, m), 7.25-7.29 (4H, m). mp (bis oxalate salt): 215°-218° C. Anal. C$_{25}$H$_{30}$N$_2$O$_9$F$_2$) C, H, N.

2-Oxo-4-[4-[bis(4-fluorophenyl)methoxy]butyl]piperazine (27 was prepared as described for 3 except 1.1 equiv. of amine used to give the title compound 27 (40%) as a slightly yellow oil. $^1$H NMR (CDCl$_3$): δ 1.57-1.69 (4H, m), 2.41 (2H, t, J=7.0), 2.60 (2H, t, J=5.4), 3.10 (2H, s), 3.31-3.35 (2H, m), 3.43 (2H, J=6.0), 5.29 (1H, s), 6.97-7.04 (4H, m), 7.07 (1H, br s), 7.25-7.30 (4H, m). mp (oxalate salt): 120°-123° C. Anal. C$_{23}$H$_{26}$N$_2$O$_6$F$_2$) C, H, N.

2-Phenyl-4-[4-[bis(4-fluorophenyl)methoxy]butyl]piperazine (28) was prepared as described for 3 except 1.1 equiv. of amine used to give the title compound 28 (63%) as a colorless oil. $^1$H NMR (CDCl$_3$): δ 1.57-1.65 (4H, m), 1.85 (1H, br), 1.97 (1H, t, J=10.6), 2.12 (1H, td, J=3.9, 10.6), 2.36 (2H, t, J=7.1), 2.84-2.92 (2H, m), 2.99-3.19 (2H, m), 3.41 (2H, t, J=5.8), 3.58 (1H, dd, J=2.6, 10.2), 5.26 (1H, s), 6.94-7.01 (4H, m), 7.21-7.39 (9H, m). mp (oxalate salt): 89°-93° C. Anal. (C$_{30}$H$_{33}$N$_2$O$_7$F$_2$) C, H, N.

1-Phenyl-4-[4-[bis(4-fluorophenyl)methoxy]butyl]piperazine (29) was prepared as described for 3 except 1.1 equiv. of amine used to give the title compound 29 (82%) as a colorless oil. $^1$H NMR (CDCl$_3$): δ 1.61-1.69 (4H, m), 2.39 (2H, t, J=7.5), 2.58 (4H, t, J=5.0), 3.20 (4H, t, J=5.3), 3.44 (2H, t, J=5.8), 5.29 (1H, s), 6.58 (1H, td, J=1.0, 6.5), 6.93 (2H, dd, J=1.0, 8.5), 6.98-7.03 (4H, m), 7.24-7.30 (6H, m). mp (oxalate salt): 185°-187° C. Anal. (C$_{29}$H$_{32}$N$_2$O$_5$F$_2$) C, H, N.

1-2-Fluorophenyl)-4-[4-[bis(4-fluorophenyl)methoxy]butyl]piperazine (30) was prepared as described for 3 except 1.1 equiv. of amine used to give the title compound 30 (83%) as a colorless oil. $^1$H NMR (CDCl$_3$): δ 1.61-1.72 (4H, m), 2.40 (2H, t, J57.1), 2.61 (4H, t, J=4.7), 3.11 (4H, t, J=4.7), 3.44 (2H, t, J=5.9), 5.29 (1H, s), 6.90-7.07 (8H, m), 7.24-7.31 (4H, m). mp (oxalate salt): 156°-158° C. Anal. (C$_{29}$H$_{31}$N$_2$O$_5$F$_3$) C, H, N.

1-(4-Fluorophenyl)-4-[4-[bis(4-fluorophenyl)methoxy]butyl]piperazine (31) was prepared as described for 3 except 1.1 equiv. of amine used to give the title compound 31 (82%) as a colorless oil. $^1$H NMR (CDCl$_3$): δ 1.63-1.70 (4H, m), 2.39 (2H, t, J=7.2), 2.58 (4H, t, J=5.0), 3.11 (4H, t, J=5.0), 3.44 (2H, t, J=5.9), 5.29 (1H, s), 6.84-7.03 (8H, m), 7.26-7.30 (4H, m). mp (oxalate salt): 177°-179° C. Anal. (C$_{29}$H$_{31}$N$_2$O$_5$F$_3$) C, H, N.

1-(2-Chlorophenyl)-4-[4-[bis(4-fluorophenyl)methoxy]butyl]piperazine (32) was prepared as described for 3 except 1.1 equiv. of amine used to give the title compound 32 (80%) as a colorless oil. $^1$H NMR (CDCl$_3$): δ 1.60-1.70 (4H, m), 2.42 (2H, t, J=7.3), 2.63 (4H, br), 3.08 (4H, br), 3.44 (2H, t, J=5.8), 5.32 (1H, s), 6.95 (1H, td, J=1.5, 7.8), 6.98-7.02 (4H, m), 7.04 (1H, dd, J=1.5, 8.0), 7.21 (1H, td, J=1.2, 7.6), 7.26-7.30 (4H, m), 7.34 (1H, dd, J=1.8, 8.3). mp (oxalate salt): 167°-169° C. Anal. (C$_{29}$H$_{31}$N$_2$O$_5$F$_2$Cl) C, H, N.

1-(3-Chlorophenyl)-4-[4-[bis(4-fluorophenyl)methoxy]butyl]piperazine (33) was prepared as described for 3 except 1.1 equiv. of amine used to give the title compound 33 (81%) as a colorless oil. $^1$H NMR (CDCl$_3$): δ 1.60-1.70 (4H, m), 2.39 (2H, t, J-7.5), 2.56 (4H, t, J=5.3), 3.19 (4H, t, J=5.0), 3.44 (2H, t, J=5.8), 5.29 (1H, s), 6.78 (2H, td, J=2.0, 9.4), 6.87 (1H, t, J=2.3), 6.98-7.03 (4H, m), 7.15 (1H, t, J=8.0), 7.26-7.30 (4H, m). mp (oxalate salt): 192°-194° C. Anal. (C$_{29}$H$_{31}$N$_2$O$_5$F$_2$Cl) C, H, N.

1-(4-Chlorophenyl)-4-[4-[bis(4-fluorophenyl)methoxy]butyl]piperazine (34) was prepared as described for 3 except 1.1 equiv. of amine used to give the title compound 34 (79%) as a colorless oil. $^1$H NMR (CDCl$_3$): δ 1.59-1.70 (4H, m), 2.39 (2H, t, J=7.5), 2.58 (4H, t, J=5.0), 3.16 (4H, t, J=5.0), 3.44 (2H, t, J=6.0), 5.29 (1H, s), 6.83 (2H, dt, J=2.8, 9.5), 6.98-7.03 (4H, m), 7.20 (2H, dt, J=2.8, 8.5), 7.26-7.30 (4H, m). mp (oxalate salt): 179°-181° C. Anal. (C$_{19}$H$_{31}$N$_2$O$_5$F$_2$Cl) C, H. N.

1-(2-Methoxyphenyl)-4-[4-[bis(4-fluorophenyl)methoxy]butyl]piperazine (35) was prepared as described for 3 except 1.1 equiv. of amine used to give the title compound 35 (78%) as a colorless oil. $^1$H NMR (CDCl$_3$): δ 1.63-1.69 (4H, m), 2.41 (2H, t, J=7.3), 2.64 (4H, br), 3.09 (4H, br), 3.44 (2H, t, J=5.8), 3.83 (3H, s), 5.31 (1H, s), 6.84 (1H, dd, J=1.0, 8.0), 6.89-7.01 (7H, m), 7.26-7.29 (4H, m). mp (oxalate salt): 139°-142° C. Anal. (C$_{30}$H$_{34}$N$_2$O$_6$F$_2$) C, H, N.

1-[3-(Trifluoromethyl)phenyl]-4-[4-[bis(4-fluorophenyl)methoxy]butyl]piperazine (36) was prepared as described for 3 except 1.1 equiv. of amine used to give the title compound 36 (79%) as a colorless oil. $^1$H NMR (CDCl$_3$): δ 1.62-1.70 (4H, m), 2.39 (2H, t, J=7.1), 2.57 (4H, t, J=4.9), 3.22 (4H, t, J=5.0), 3.45 (2H, t, J=5.9), 5.29 (1H, s), 6.96-7.11 (7H, m), 7.26-7.34 (5H, m). mp (oxalate salt): 188°-190° C. Anal. (C$_{30}$H$_{31}$N$_2$O$_5$F$_5$) C, H, N.

1-[4-[4-[4-[Bis(4-fluorophenyl)methoxy]butyl]piperazin-1-yl]phenyl]ethanone (37) was prepared as described for 3 except 1.1 equiv. of amine used to give the title compound 37

(82%) as a slightly yellow solid. $^1$H NMR (CDCl$_3$): δ 1.62-1.69 (4H, m), 2.39 (2H, t, J=7.5), 2.51 (3H, s), 2.56 (4H, t, J=5.3), 3.35 (4H, t, J=5.0), 3.45 (2H, t, J=6.0), 5.30 (1H, s), 6.86 (2H, d, J=9.5), 6.99-7.02 (4H, m), 7.26-7.30 (4H, m), 7.87 (2H, d, J=9.0). mp (oxalate salt): 185°-187° C. Anal. (C$_{31}$H$_{34}$N$_2$O$_6$F$_2$) C, H, N.

1-[4-Nitrophenyl]-4-[1-[bis(4-fluorophenyl)methoxy]-4-butyl]piperazine (38) was prepared as described for 3 except 1.1 equiv. of amine used to give the title compound 38 (76%) as a colorless oil. $^1$H NMR (CDCl$_3$): δ 1.50-1.71 (4H, m), 2.39 (2H, t, J=7.5), 2.55 (4H, t, J=5.3), 3.40 (4H, t, J=5.3), 3.45 (2H, t, J=6.3), 5.30 (1H, s), 6.80 (2H, dt, J=2.9, 9.5), 6.98-7.03 (4H, m), 7.26-7.31 (4H, m), 8.10 (2H, dt, J=2.9, 9.5). mp (oxalate salt): 196°-198° C. Anal. (C$_{29}$H$_{31}$N$_3$O$_7$F$_2$) C, H, N.

1-[4-[Bis(4-fluorophenyl)methoxy]butyl]-4-pyridin-2-ylpiperazine (39) was prepared as described for 3 except 1.1 equiv. of amine used to give the title compound 39 (79%) as a colorless oil. $^1$H NMR (CDCl$_3$): δ 1.62-1.69 (4H, m), 2.38 (2H, t, J=7.3), 2.53 (4H, t, J=5.3), 3.44 (2H, t, J=6.0), 3.54 (4H, t, J=5.3), 5.29 (1H, s), 6.60 (1H, dd, J=5.3, 6.8), 6.63 (1H, d, J=8.5), 6.98-7.02 (4H, m), 7.26-7.29 (4H, m), 7.45 (1H, tt, J=2.2, 7.9), 8.18 (1H, dd, J=1.5, 5.0). mp (oxalate salt): 174°-176° C. Anal. (C$_{28}$H$_{31}$N$_3$O$_5$F$_2$) C, H, N.

1-Benzoyl-4-[1-[bis(4-fluorophenyl)methoxy]-4-butyl]piperazine (40) Benzoyl chloride was dissolved in 10 mL of anhydrous CH$_2$Cl$_2$ and was added dropwise to the mixture of 3 (360 mg, 1 mmol) and triethylamine (304 mg, 3 mmol) in 20 mL of anhydrous CH$_2$Cl$_2$. The reaction mixture was allowed to stir for 2 h at ambient temperature. The solvent was removed using rotary evaporation. Ethyl acetate (200 mL) and saturated NaCl solution (30 mL) were added to the resultant crude product and stirred 2 h. The organic layer was separated, washed with sat. NaCl (30 mL), dried over MgSO$_4$, filtered and evaporated to dryness. The crude product was purified by chromatography on silica gel to give the title compound 40 (89%) as a colorless oil. $^1$H NMR (CDCl$_3$): δ 1.56-1.69 (4H, m), 2.37 (4H, t, J=7.3), 2.50 (2H, br s), 3.43 (4H, t, J=6.0), 3.79 (2H, br s), 5.28 (1H, s), 6.98-7.02 (4H, m), 7.25-7.29 (4H, m), 7.38-7.42 (5H, m). mp (oxalate salt): 121°-123° C. Anal. (C$_{30}$H$_{32}$N$_2$O$_6$F$_2$) C, H, N.

1-Benzo[1,3]dioxol-5-ylmethyl-4-[4-[bis(4-fluorophenyl)methoxy]butyl]piperazine (41) was prepared as described for 3 except 1.1 equiv. of amine and 1.0 equiv. of piperonyl chloride as alkylating agent used to give the title compound 41 (79%) as a colorless oil. $^1$H NMR (CDCl$_3$): δ 1.55-1.67 (4H, m), 2.33 (4H, t, J=7.3), 2.45 (6H, br s), 3.40 (2H, s), 3.41 (2H, t, J=6.8), 5.27 (1H, s), 5.90 (2H, s), 6.73 (2H, d, J=1.0), 6.85 (1H, s), 6.96-7.01 (4H, m), 7.25-7.28 (4H, m). mp (oxalate salt): 231°-234° C. Anal. (C$_{33}$H$_{36}$N$_2$O$_{11}$F$_2$) C, H, N.

1-[4-[Bis(4-fluorophenyl)methoxy]butyl]-4-(4-nitrobenzenesulfonyl)piperazine (42) was prepared as described for 40 to give the title compound 42 (75%) as a colorless oil. $^1$H NMR (CDCl$_3$): δ 1.49-1.54 (2H, m), 1.56-1.62 (2H, m), 2.33 (2H, t, J=7.3), 2.50 (4H, br t, J=4.5), 3.06-3.07 (4H, m), 3.38 (2H, t, J=6.5), 5.25 (1H, s), 6.96-7.01 (4H, m), 7.23-7.27 (4H, m), 7.93-7.95 (2H, m), 8.37-8.39 (2H, m). mp (oxalate salt): 170°-173° C. Anal. (C$_{29}$H$_{31}$N$_3$O$_9$F$_2$S) C, H, N.

Biological Methods.

1. Methods for In Vitro Binding and Reuptake Inhibition Assay. In vitro assays for [$^{125}$I]RTI-55 binding inhibition and [$^3$H] neurotransmitter uptake inhibition for HEK 293 cells expressing recombinant biogenic amine transporters were carried out according to the procedures described previously. (Biog. Med. Chem. Lett. 1997, 7, 2559-2564 and J. Pharmacol. Exp. Ther., 1999, 289, 877-885)

2. Methods for In Vitro Receptor Binding and Functional Biochemical Assays. Receptor Binding Assay Method: 5-HT$_{1A}$ Receptor: HA7 cells (human receptor) are grown to confluence in DMEM containing 10% fetal calf serum, 0.05% penicillin-streptomycin (pen-strep), and 400 μg/ml of G418. The cells are scraped from the 100×20 mm plates and centrifuged at 500×g for 5 min. The pellet is homogenized in 50 mM Tris-HCl pH 7.7, with a polytron, centrifuged at 27,000×g and resuspended at 10 mg protein/ml in the same buffer. The homogenate is then stored at −70° C. in 1-ml aliquots. The thawed cells are washed once and resuspended at 10 mg protein/80 ml in 25 mM Tris-HCl containing 100 μM of ascorbic acid and 10 μM of nialamide at pH 7.4. The assay is performed in triplicate in a 96-well plate. To 100 μl of [$^3$H]8-OH-DPAT (0.5 nM final conc.), 100 μl of test compound or buffer and 0.8 ml of cell homogenate (0.1 mg protein/well) is added to each well by a Tomtec Quadra 96. Nonspecific binding is defined using 1 μM dihydroergotamine. The plates are incubated at 25° C. for 60 min, then filtered. The incubation is terminated by rapid filtration through glass fiber filter paper on a Tomtec cell harvester. The filters are washed four times with ice-cold 50 mM Tris-HCl, pH 7.7, dried overnight, bagged with 10 ml scintillation cocktail before counting for 2 min. on a Wallac Betaplate 1205 liquid scintillation counter. 5-HT$_{2C}$ Receptor: NIH-3T3-Pφ cells (rat receptor) are grown and prepared in the same manner as the HA7 cells. The final pellet is resuspended at 3 mg protein/80 ml of 50 mM Tris-HCl, pH 7.7, 4 mM of CaCl$_2$, 10 μM pargyline, and 0.1% ascorbic acid. Wells containing 100 μl of test drug or buffer, 100 μl of [$^3$H]mesulergine (0.4 nM final conc.), and 0.8 ml of cell homogenate (0.03 mg protein/well) are incubated at 25° C. for 60 min. Mesulergine is used at 10 μM to determine nonspecific binding. 5-HT$_{2A}$ Receptor: NIH-3T3-GF6 cells (rat receptor) are grown as described for HA7 cells. On the day of the experiment the cells are thawed, resuspended in 50 mM Tris-HCl, and centrifuged at 27,000×g for 12 min. The pellet is then resuspended at 1 mg protein/80 ml of 25 mM Tris-HCl, pH 7.7, and 0.8 ml of cell homogenate (0.01 mg protein/well) is added to wells containing 100 μl of the test drug or buffer and 100 μl of [$^3$H]ketanserin (0.40 nM final conc.). The plates are incubated at 25° C. for 60 min. Nonspecific binding is determined with 1 μM of ketanserin. 5-HT$_3$ Receptor: NG108-15 cells (rat/mouse hybrid) are grown to confluence on 100×20 mm plates in DMEM with HAT supplement and 10% fetal calf serum. The cells are washed from the plates, centrifuged, homogenized as described above, and stored at −70° C. in aliquots of 15 plates/4 ml. The thawed cells are washed once and resuspended at 15 plates/20 ml of 25 mM Tris-HCl, pH 7.7. The assay is performed by adding 50 μl of test drug or buffer, 50 μl of [$^3$H]GR65630 (1.6 nM final conc.), and 0.4 ml of cell homogenate (0.13 mg protein/tube) to each tube. The tubes are then incubated at 25° C. for 45 min. Nonspecific binding is defined by 1 μM of zacopride. Filters are soaked in 0.1% PEI (polyethylenimine) before filtering. The incubation is terminated by rapid filtration through Whatman GF/B filter paper on a Brandel cell harvester. The filters are washed three times with ice-cold 50 mM Tris-HCl, pH 7.7, and soaked overnight in scintillation cocktail before counting for 2 min. on a Beckman LS 6000. D$_1$ Receptor: LHD$_1$ cells (human receptor) are grown and prepared as described for the HA7 cells. The final pellet is resuspended at 5 mg protein/80 ml in 50 mM Tris-HCl containing 120 mM of NaCl, 5 mM of KCl, 2 mM of CaCl$_2$, and 1 mM of MgCl$_2$, pH 7.4. To wells containing 100 μl of test drug or buffer and 100 μl of [$^3$H]SCH 23,390 (0.18 mM final conc.), is added 0.8 ml of cell homogenate (0.05 mg protein/well), and the plates are incubated at 25° C. for 60 min. Nonspecific binding is determined with 1 µM of SCH 23,390. $D_2$ and $D_3$ Receptors: CHOp-cells human receptors are grown to confluence in α minimum essential medium (α MEM) containing 10% fetal calf serum, 0.05% pen-strep, and 600 µg/ml of G418. The cells are scraped from the 100×20 mm plates and centrifuged at 500×g for 5 min. The pellet is homogenized by polytron in 50 mM Tris-HCl, pH 7.7, and centrifuged at 27,000×g for 12 min. The pellet is resuspended in 50 mM Tris, $D_2$ at 5 mg protein/ml, $D_3$ at 1 mg protein/ml, and stored at −70° C. in 1-ml aliquots. On the day of the experiment, CHOp-$D_2$ or CHOp-$D_3$ cells are thawed, resuspended in 50 mM Tris, and centrifuged at 27,000×g for 12 min. The pellet is then resuspended at 5 mg protein/80 ml ($D_2$) and 1 mg protein/80 ml ($D_3$) in 50 mM Tris containing 120 mM of NaCl, 5 mM of KCl, 1.5 mM of $CaCl_2$, and 4 mM of $MgCl_2$, and 1 mM of EDTA, pH 7.4. Then 0.8 ml of cell homogenate (0.05 and 0.01 mg protein/well, $D_2$ and $D_3$ respectively) is added to wells containing 100 µl of test drug or buffer and 100 µl of [$^3$H]YM-09151-2 (0.12 nM final conc.). Nonspecific binding is determined with 1 µM of chlorpromazine. The plates are incubated at 25° C. for 60 min before filtration and counted as usual. The filters are soaked in 0.1% PEI before filtering. Functional Biochemical Assay: Antagonist Potencies for Inhibition of 10 mM Quinpirole Stimulation of Mitogenesis in CHOp-$D_2$ and -$D_3$ Cells: To measure $D_2$ and $D_3$ stimulation of mitogenesis, CHOp-cells (human receptor) are used in a 96-well plate containing approximately 5,000 cells/well. The cells are incubated at 37° C. in a minimum essential medium (a MEM) with 10% FBS (fetal bovine serum), 0.05% pen-strep, and 200 µg/ml Geneticin (G418 sulfate). After 48 h, the wells are rinsed twice with 100-µl aliquots of serum-free α-MEM and incubated for 24 hr at 37° C. in serum-free α-MEM. The medium is then removed and replaced with 90 µl of serum-free α-MEM and 10 µl of drug in sterile water. After another 24 hr of incubation at 37° C., 0.25 µCi of [$^3$H]thymidine is added to each well. The cells are incubated for 2 hr at 37° C. Then, 10 µl/well of 10× trypsin (trypsin-EDTA solution: 5 g trypsin in 20 ml) is added to remove the cells, and the plates are filtered using a Tomtec cell harvester. The filters are washed 4 times with deionized water, dried overnight, bagged with 10 ml scintillation cocktail before counting for 2 min. on a Wallac Betaplate 1205 liquid scintillation counter. Quinpirole is run on every plate as an internal standard.

3. Locomotor Activity. The study was conducted using 16 Digiscan locomotor activity testing chambers (40.5×40.5×30.5 cm). Panels of infrared beams (16 beams) and corresponding photodetectors were located in the horizontal direction along the sides of each activity chamber. Separate groups of 8 non-habituated male Swiss-Webster mice were injected via the intraperitoneal (IP) route with either vehicle (methylcellulose or saline or distilled water) or compound (3, 10, 30, or 100 mg/kg), 20 minutes prior to locomotor activity testing. Just prior to placement in the apparatus, all mice received a saline injection IP. In all studies, horizontal activity (interruption of 1 photocell beam) was measured for 1-h within 10-min periods. Testing was conducted with one mouse per activity chamber. For cocaine/compound interaction study, twenty minutes following IP vehicle or compound injections (3, 10, 30, or 100 mg/kg), groups of 8 non-habituated male Swiss-Webster mice were injected with either 0.9% saline or 20 mg/kg cocaine IP and placed in the Digiscan apparatus for a 1-h session. Maximal effects of cocaine and stimulant test compound (cocaine and test compound alone studies): Pick one 30 min time period in which maximal effects are evident at most doses. Plot the mean (±SEM) maximal stimulant activity (total counts in the 30 min period divided by 3) vs dose. Perform a $log_{10}$ transformation of the 30 min period average counts for individual subjects to homogenize variances for subsequent analyses. Conduct an ANOVA and contrast (specified a priori) each dose of cocaine (the test compound) to saline (to the vehicle) to determine significant (p<0.05) dose effects. Fit the 30 min period average counts across subjects to a function of $log_{10}$ dose using least-squares curve-fitting analyses (i.e. TableCurve software from Jandel). Estimate the maximum effect from the resultant dose-response curve. Determine a test compound maximal effect/cocaine maximum effect (ME/CME) ratio. Determine the $ED_{50}$ (dose that produces ½ maximal stimulant activity) from a linear regression analysis of the ascending portion (up to the dose that produces a maximal effect) of the curve. Calculate the mean maximal effect for cocaine each month. Maximal Effects of Depressant Test Compound (test compound alone studies): Pick one 30 min time period in which cocaine (20 mg/kg) produces its maximal effects as determined from the cocaine alone studies. Plot the mean (±SEM) activity (total counts in the 30 min period divided by 3) vs dose. Perform a $log_{10}$ transformation of the 30 min period average counts for individual subjects to homogenize variances for subsequent analyses. Conduct an ANOVA and contrast (specified a priori) each dose of the test compound to the vehicle to determine significant (p<0.05) dose effects. Conduct a linear least-squares regression analysis; regress the 30 min period average counts across subjects over the descending potion of the curve against the $log_{10}$ dose of the test compound. Determine the $ID_{50}$ (dose that produces ½ maximal depressant activity where maximum depression=0) from the linear regression analysis. Maximal Effects of Test Compound/Cocaine Interaction Studies: Pick one 30 min time period in which cocaine (20 mg/kg) produces its maximal activity as determined from the cocaine alone studies. Plot the mean (±SEM) maximal activity (total counts in the 30 min period divided by 3) for vehicle, vehicle part+cocaine (20 mg/kg) and test compound pretreatment+cocaine (20 mg/kg) data in a histogram. Perform a $log_{10}$ transformation of the 30 min period average counts for individual subjects to homogenize variances for subsequent analyses. Conduct an ANOVA and contrast (specified a priori) vehicle and each dose of the test compound+cocaine to cocaine alone to determine significant (p<0.05) dose effects. Conduct a linear least-squares regression analysis; regress the 30 min period average counts across subjects over the descending potion of the curve against the $log_{10}$ dose of the test compound. Determine the $AD_{50}$ (dose that attenuates cocaine-induced stimulation by 50%) from the linear regression analysis. Locomotor Activity 8-Hour Time Course/Dose Response Study. Cocaine Alone Study. The study was conducted using 40 Digiscan locomotor activity testing chambers (40.5×40.5×30.5 cm) housed in sets of two, within sound-attenuating chambers. A panel of infrared beams (16 beams) and corresponding photodetectors were located in the horizontal direction along the sides of each activity chamber. A 7.5-W incandescent light above each chamber provided dim illumination. Fans provided an 80-dB ambient noise level within the chamber. Separate groups of 8 non-habituated male Swiss-Webster mice (Hsd:ND4, aged 2-3 mo.) were injected via the intraperitoneal (IP) route with either vehicle (methylcellulose or saline or distilled water) or compound (3, 10, 30, or 100 mg/kg), 20 minutes prior (for cocaine, immediately prior to) to locomotor activity testing. In all studies, horizontal activity (interruption of photocell beams) was measured for 8-h within 10-min periods, beginning at 0800 hrs (2 hours after lights on). Testing was conducted with one mouse per activity chamber. Compound Alone Study. A time course/dose response study of test compound-induced locomotor depression/stimulation was conducted under the same conditions as outlined for the cocaine alone study described above. Separate groups of 8 mice were injected with either vehicle (methylcellulose or saline or distilled water) or test compound (1, 3, 10, 30, or 100 mg/kg), immediately prior to locomotor activity testing.

Elemental Analysis:

1-[1-[bis(4-fluorophenyl)methoxy]butyl]piperazine (3)
  Anal. Calcd for $C_{25}H_{30}N_2O_9F_2$: C, 55.55; H, 5.59; N, 5.18. Found: C, 55.41; H, 5.56; N, 5.12.

2-Ozo-4-[4-[bis(4-fluorophenyl)methoxy]butyl]piperazine (27)
  Anal. Calcd for $C_{23}H_{26}N_2O_6F_2$: C, 59.48; H, 5.64; N, 6.03. Found: C, 59.22; H, 5.73; N, 5.99.

2-Phenyl-4-[4-[bis(4-fluorophenyl)methoxy]butyl]piperazine (28)
  Anal. Calcd for $C_{30}H_{33}N_2O_7F_2$: C, 62.93; H, 5.99; N, 4.89. Found: C, 62.91; H, 6.07; N, 491.

1-Phenyl-4-[4-[bis(4-fluorophenyl)methoxy]butyl]piperazine (29)
  Anal. Calcd for $C_{29}H_{32}N_2O_5F_2$: C, 66.15; H, 6.13; N, 5.32. Found: C, 66.03; H, 6.09; N, 5.31.

1-(2-Fluorophenyl)-4-[4-[bis(4-fluorophenyl)methoxy]butyl]piperazine (30)
  Anal. Calcd for $C_{29}H_{31}N_2O_5F_3$: C, 63.96; H, 5.74; N, 5.14. Found: C, 64.12; H, 5.79; N, 5.16.

1-(4-Fluorephenyl)-4-[4-[bis(4-fluorophenyl)methoxy]butyl]piperazine (31)
  Anal. Calcd for $C_{29}H_{31}N_2O_5F_3$: C, 63.96; H, 5.74; N, 5.14. Found: C, 64.16; H, 5.82; N, 5.11.

1-(2-Chlorophenyl)-4-[4-[bis(4-fluorophenyl)methoxy]butyl]piperazine (32)
  Anal. Calcd for $C_{29}H_{31}N_2O_5F_2Cl$: C, 62.09; H, 5.57; N, 4.99. Found: C, 6220; H, 5.64; N, 4.93.

1-(3-Chlorophenyl)-4-[4-[bis(4-fluorophenyl)methoxy]butyl]piperazine (33)
  Anal. Calcd for $C_{29}H_{31}N_2O_5F_2Cl$: C, 62.09; H, 5.57; N, 4.99. Found: C, 62.17; H, 5.50; N, 5.02.

1-(4-Chlorophenyl)-4-[4-[bis(4-fluorophenyl)methoxy]butyl]piperazine (34)
  Anal. Calcd for $C_{29}H_{31}N_2O_5F_2Cl$: C, 62.09; H, 5.57; N, 4.99. Found: C, 61.88; H, 5.58; N, 4.93.

1-(2-Methoxyphenyl)-4-[4-[bis(4-fluorophenylmethoxy]butyl]piperazine (35)
  Anal. Calcd for $C_{30}H_{34}N_2O_6F_2$: C, 64.74; H, 6.16; N, 5.03. Found: C, 64.70; H, 6.15; N, 5.03.

1-[3-(Trifluoromethyl)phenyl]-4-[4-[bis(4-fluorophenyl)methoxy]butyl]piperazine (36)
  Anal. Calcd for $C_{30}H_{31}N_2O_5F_5$: C, 60.60; H, 5.26; N, 4.71. Found: C, 60.67; H, 5.25; N, 4.71.

1-[4-[4-[1-[Bis(4-fluorophenyl)methoxy]-4-butyl]piperazin-1-yl]phenyl]ethane-1-one (37)
  Anal. Calcd for $C_{31}H_{34}N_2O_6F_2$: C, 65.48; H, 6.03; N, 4.93. Found: C, 65.50; H, 6.04; N, 4.92.

1-[4-Nitrophenyl]-4-[1-[bis(4-fluorophenyl)methoxy]-4-butyl]piperazine (38)
  Anal. Calcd for $C_{29}H_{31}N_3O_7F_2$: C, 60.94; H, 5.47; N, 7.35. Found: C, 60.64; H, 5.56; N, 7.16.

1-[4-[1-Bis(4-fluorophenyl)methoxy]butyl]-4-pyridin-2-ylpiperazine (39)
  Anal. Calcd for $C_{28}H_{31}N_3O_5F_2$: C, 58.34; H, 5.39; N, 6.80. Found: C, 58.74; H, 5.49; N, 6.84.

1-Benzoyl-4-[1-[bis(4-fluorophenyl)methoxy]-4-butyl]piperazine (40)
  Anal. Calcd for $C_{31}H_{36}N_2O_7F_2$: C, 63.47; H, 6.19; N, 4.78. Found: C, 63.33; H, 5.99; N, 4.82.

1-Benzo[1,3]dioxol-5-ylmethyl-4-[4-[bis(4-fluorophenyl)methoxy]butyl]piperazine (41)
  Anal. Calcd for $C_{33}H_{36}N_2O_{11}F_2$: C, 58.75; H, 5.38; N, 4.15. Found: C, 58.66; H, 5.34; N, 4.13.

1-[4-[Bis(4-fluorophenyl)methoxy]butyl]-4-(4-nitrobenzenesulfonyl)piperazine (42)
  Anal. Calcd for $C_{29}H_{31}N_3O_9F_2S$: C, 54.80; H, 4.92; N, 6.61. Found: C, 54.50; H, 4.95; N, 6.45.

TABLE 5

Binding Affinities and Selectivities of Bisarylmethoxybutylpiperazine derivatives at the DA, 5-HT and NE Transporters Labeled with [$^{125}$I]RTI-55 (Ki ± SD, nM)[a]

| Compound | Binding | | | Ratios | |
| --- | --- | --- | --- | --- | --- |
| | DAT | SERT | NET | SERT/DAT | NET/DAT |
| 3 | 600 ± 190 | 1900 ± 330 | 3400 ± 1500 | 3.2 | 5.7 |
| 27 | 4100 ± 790 | 1800 ± 450 | >10 μM | 0.4 | >2.4 |
| 28 | 3.81 ± 0.84 | 74.6 ± 5.8 | 190 ± 50 | 19.6 | 49.9 |
| 29 | 60.9 ± 6.4 | 51 ± 18 | 203 ± 76 | 0.8 | 3.3 |
| 30 | 38.7 ± 5.6 | 30.0 ± 8.4 | 417 ± 34 | 0.8 | 10.8 |
| 31 | 26.5 ± 3.0 | 34 ± 12 | 207 ± 20 | 1.3 | 7.8 |
| 32 | 67 ± 10 | 88 ± 29 | 540 ± 180 | 1.3 | 8.1 |
| 33 | 175 ± 71 | 148 ± 62 | 300 ± 70 | 0.8 | 1.7 |
| 34 | 50 ± 12 | 33 ± 11 | 380 ± 130 | 0.7 | 7.6 |
| 35 | 26.2 ± 2.5 | 255 ± 89 | 92 ± 11 | 9.7 | 3.5 |
| 36 | 32.5 ± 4.1 | 222 ± 80 | 222 ± 9.7 | 6.8 | 6.8 |
| 37 | 27.0 ± 8.6 | 42 ± 16 | 112 ± 38 | 1.6 | 4.1 |
| 38 | 60 ± 19 | 154 ± 44 | 239 ± 13 | 2.6 | 4.0 |
| 39 | 8.4 ± 4.0 | >10 μM | 103 ± 37 | >1190 | 12.3 |
| 40 | 19.7 ± 2.5 | 87 ± 43 | 365 ± 69 | 4.4 | 18.5 |
| 41 | 33 ± 13 | 59 ± 22 | 55 ± 18 | 1.8 | 1.7 |
| 42 | 760 ± 220 | 4930 ± 670 | >10 μM | 6.5 | >13.2 |
| GBR 12909 | 27 ± 8 | 186 ± 30 | 163 ± 39 | 6.9 | 6.0 |
| cocaine | 450 ± 150 | 308 ± 33 | 1640 ± 140 | | |
| cocaine[b] | 915 ± 214 | 419 ± 12 | 600 ± 216 | | |
| cocaine[c] | 271 ± 65 | 217 ± 23 | 1730 ± 280 | | |
| cocaine[d] | 258 ± 23 | 343 ± 31 | 1740 ± 180 | | |
| cocaine[e] | 573 ± 54 | 402 ± 62 | 2040 ± 240 | | |

TABLE 5-continued

Binding Affinities and Selectivities of Bisarylmethoxybutylpiperazine derivatives at the DA, 5-HT and NE Transporters Labeled with [$^{125}$I]RTI-55 (Ki ± SD, nM)$^a$

|  | Binding | | | Ratios | |
| --- | --- | --- | --- | --- | --- |
| Compound | DAT | SERT | NET | SERT/DAT | NET/DAT |
| cocaine$^f$ | 350 ± 45 | 260 ± 9.4 | 1610 ± 300 | | |
| cocaine$^g$ | 621 ± 45 | 496 ± 37 | 1400 ± 320 | | |

$^a$Results are average ± SEM of three independent experiments assayed in triplicate.
$^b$Cocaine as reference for GBR 12909,
$^c$for 27, 28, 30, 31, 36
$^d$for 29, 33, 34, 35,
$^e$for 32,
$^f$for 39,
$^g$for 42.

TABLE 6

DA, 5-HT and NE Reuptake Inhibition and Ratios of Reuptake to binding of Bisarylmethoxybutylpiperidine/piperazine derivatives at the DA Transporters (IC$_{50}$ ± SD, nM)$^a$

| Compound | Reuptake Inhibition (IC$_{50}$ ± SD, nM) | | | Discrimination Ratios [$^3$H]DA reuptake/ DAT binding |
| --- | --- | --- | --- | --- |
| | [$^3$H]DA | [$^3$H]5-HT | [$^3$H]NE | |
| 3 | 1000 ± 190 | 2170 ± 78 | 850 ± 270 | 1.7 |
| 27 | 2290 ± 200 | 5340 ± 950 | >10 μM | 0.6 |
| 28 | 550 ± 140 | 700 ± 260 | 290 ± 50 | 144.4 |
| 29 | 1410 ± 580 | 1020 ± 320 | 56.3 ± 9.4 | 23.2 |
| 30 | 460 ± 140 | 192 ± 21 | 700 ± 240 | 11.9 |
| 31 | 610 ± 150 | 440 ± 50 | 225 ± 28 | 23 |
| 32 | 328 ± 34 | 119 ± 33 | 290 ± 110 | 4.9 |
| 33 | 1670 ± 440 | 920 ± 420 | 189 ± 89 | 9.5 |
| 34 | 1170 ± 250 | 320 ± 120 | 390 ± 130 | 23.4 |
| 35 | 301 ± 16 | 1233 ± 24 | 176 ± 79 | 11.5 |
| 36 | 380 ± 130 | 3300 ± 1300 | 310 ± 100 | 11.7 |
| 37 | 3010 ± 8.6 | 1230 ± 540 | 33 ± 15 | 111.5 |
| 38 | 2350 ± 540 | 390 ± 130 | 230 ± 110 | 39.2 |
| 39 | 386 ± 55 | >10 μM | 2230 ± 710 | 46 |
| 40 | 640 ± 240 | 2170 ± 370 | 32 ± 10 | 32.5 |
| 41 | 1000 ± 60 | 3280 ± 610 | 43 ± 19 | 30.3 |
| 42 | 4200 ± 1100 | >10 μM | >10 μM | 5.5 |
| GBR 12909 | 246 ± 142 | 584 ± 237 | 532 ± 183 | 9.1 |
| cocaine | 393 ± 53 | 280 ± 57 | 238 ± 46 | |
| cocaine$^b$ | 915 ± 214 | 419 ± 12 | 600 ± 216 | |
| cocaine$^c$ | 278 ± 53 | 189 ± 31 | 209 ± 36 | |
| cocaine$^d$ | 276 ± 22 | 301 ± 53 | 264 ± 57 | |
| cocaine$^e$ | 237 ± 41 | 348 ± 66 | 190 ± 38 | |
| cocaine$^f$ | 471 ± 35 | 405 ± 39 | 239 ± 26 | |
| cocaine$^g$ | 330 ± 18 | 415 ± 22 | 440 ± 59 | |

$^a$Results are average ± SEM of three independent experiments assayed in triplicate.
$^b$Cocaine as reference for GBR 12909,
$^c$for 27, 28, 30, 31, 36,
$^d$for 29, 33, 34, 35,
$^e$for 32,
$^f$for 39,
$^g$for 42.

TABLE 7

Receptor Binding Profile and Effects of Selected Target Compounds 28, 29, 34, 35, 39 and 40$^a$

| Receptor | Affinity (Ki ± S.D., nM)$^b$/Antagonist activity (IC$_{50}$, nM)$^c$ | | | | | |
| --- | --- | --- | --- | --- | --- | --- |
| | 28 | 29 | 34 | 35 | 39 | 40 |
| D$_1$ | 6150 ± 541 | 2430 ± 367 | >10 μM | 777 ± 185 | 597 ± 19.4 | 6640 ± 313 |
| D$_2$ | 715 ± 404 | 447 ± 73.9 | >10 μM | 134 ± 21.7 | 282 ± 67.7 | 95.5 ± 19.7 |
| | 164 ± 22.4$^c$ | 120 ± 33.0$^c$ | nt | 84.4 ± 31.8$^c$ | 196 ± 62.8$^d$ | 183 ± 33.4$^c$ |
| D$_3$ | 677 ± 262 | 242 ± 7.41 | 340 ± 143 | 118 ± 31.9 | 453 ± 163 | 119 ± 49.8 |
| | 629 ± 284$^c$ | 44.6 ± 1.76$^c$ | 2.55 ± 0.14$^c$ | 56.7 ± 26.2$^c$ | 955 ± 76$^c$ | 222 ± 38.7$^c$ |
| 5-HT$_{1A}$ | 2250 ± 359 | 285 ± 76.4 | >10 μM | 34.9 ± 6.7 | 53.5 ± 8.62 | 1560 ± 271 |
| 5-HT$_{2A}$ | 1490 ± 352 | 404 ± 52.6 | 1150 ± 44.2 | 698 ± 204 | 498 ± 47.9 | 4800 ± 2090 |
| 5-HT$_{2C}$ | 6700 ± 437 | >10 μM | >10 μM | 3000 ± 73.1 | 3450 ± 1080 | 4640 ± 586 |

$^a$All values represent the mean of at least two determinations.
$^b$Receptors and radioligands used in binding assay: D$_1$ (human cloned receptors in LHD$_1$ cells, [$^3$H]SCH 23,390); D$_2$ and D$_3$ (human cloned receptors in CHO$_P$-cells, [$^3$H]YM-09151-2); 5-HT$_{1A}$ (human cloned receptors in HA7 cells, [$^3$H]8-OH-DPAT); 5-HT$_{2A}$ (rat receptors in NIH-3T3-GF6 cells, [$^3$H]ketanserin); 5-HT$_{2C}$ (rat receptors in NIH-3T3-P$_o$ cells, [$^3$H]mesulergine); 5-HT$_3$ (rat/mouse hybrid receptors in NG108-15 cells, [$^3$H]GR65630).
$^c$D$_2$, D$_3$ antagonist assays, CHO$_p$ cells (human receptor), [$^3$H]Thymidine Incorporation, Inhibition of mitogenesis, Quinpirole as internal standard (EC$_{50}$ range 6.5-57 nM for D$_2$ receptor, EC$_{50}$ range 2.8-25 nM for D$_3$ receptor),
$^d$agonist,
nt; not tested

TABLE 8

Effects of compounds 28, 30, 36, 39 and 42 on Locomotor Activity in mouse[a]

| Compound | $ED_{50}$ (mg/kg)[b] | mode of action[c] | ME/CME[d] | $AD_{50}$ (mg/kg)[e] |
|---|---|---|---|---|
| 28 | 1.52/S[f] | monophasic | 0.30 | 50.27 |
| 30 | 0.015/S | monophasic | 0.49 | no attenuation |
| 36 | 113/I[g] | monophasic | | 18.35 |
| 39 | no activity | | | 62.1 |
| 42 | no activity | | | no attenuation |
| GBR 12909 | 6.24/S | monophasic | 1.22 | biphasic[h] |

[a,b]$ED_{50}$, dose producing ½ maximal stimulant activity.
[c]ligand alone study, see text for details, in general low doses-stimilation, high doses-inhibition.
[d]Maximal Effect (ME)/Cocaine Maximal Effect (CME).
[e]ligand-cocaine interaction study, $AD_{50}$, dose attenuating cocaine-induced stimulation by 50%.
[f]S, stimulation.
[g]$ID_{50}$, dose-producing ½ maximal depressant activity, where maximal depression = 0 count/30 min, I, inhibition.
[h]10 mg/kg enhanced and 50 mg/kg depressed during the period 30-60 min. postinjection.

TABLE 9

Effects of compounds 28, 36 and 39 on Locomotor Activity for 8 hours in mouse[a]

| Compound | $ED_{50}$ (mg/kg)[b] | mode of action[c] | ME/CME[d] |
|---|---|---|---|
| 28 | 36.4/I[e,f] 7.6/S[g,h] | biphasic | 0.30 |
| 36 | 1.1/S[h] | monophasic | 0.46 |
| 39 | 60.3/I[e,i] 38.0/S[g,j] | biphasic | >0.35 |
| GBR 12909 | 6.9/S[g] | monophasic | 0.73 |

[a,b]$ED_{50}$, dose producing ½ maximal stimulant activity.
[c]ligand alone study, see text for details.
[d]Maximal Effect (ME)/Cocaine Maximal Effect (CME).
[e]$ID_{50}$, dose-producing ½ maximal depressant activity. I, inhibition.
[f]30 mg/kg from 10 min. to 70 min. 100 mg/kg from 10 min to 90 min.
[g]S, stimulation.
[h]30 mg/kg from 90 min. to 410 min. Lethality occurred in 2/8 mice within 30 min. after 100 mg/kg.
[i]30-100 mg/kg from 10 min. to 40-50 min.
[j]100 mg/kg from 210 min. to 490 min.

The invention claimed is:

1. A method for imaging dopamine neurons in a human which comprises:
    administering to the human an imaging dose of a compound of Formula V labeled with a radionuclide; and
    detecting binding of the compound of Formula V in the human,
    wherein
      the compound of Formula V is Formula V $R_7$ is hydrogen, O or phenyl; and
$R_8$ is hydrogen, phenyl, halophenyl, nitrophenyl, pyridyl, piperonyl or sulfoxonitrophenyl.

2. A method of treating a human afflicted with cocaine abuse which comprises:
    administering to the human an effective amount of a compound of Formula V,
    wherein
      the compound of Formula V is Formula V $R_7$ is hydrogen, O or phenyl; and
$R_8$ is hydrogen, phenyl, halophenyl, nitrophenyl, pyridyl, piperonyl or sulfoxonitrophenyl.

3. A method of treating a human afflicted with Parkinson's disease which comprises:
    administering to the human an effective amount of the compound of Formula V,
    wherein
      the compound of Formula V is Formula V $R_7$ is hydrogen, O or phenyl; and
$R_8$ is hydrogen, phenyl, halophenyl, nitrophenyl, pyridyl, piperonyl or sulfoxonitrophenyl.

4. The method of claim 1, wherein the compound of Formula V is labeled with $^{99m}$Tc.

5. The method of claim 1, wherein the compound of Formula V is labeled with an iodine isotope.

6. The method of claim 1, wherein the compound of Formula V is

7. The method of claim 2, wherein the compound of Formula V is
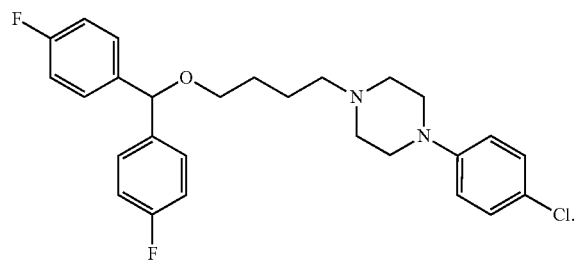
8. The method of claim 3, wherein the compound of Formula V is
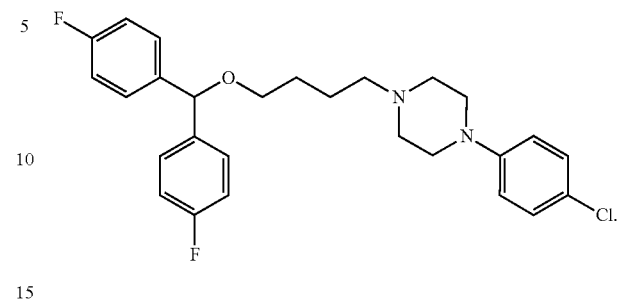
* * * * *